US010774329B2

(12) United States Patent
Sayre et al.

(10) Patent No.: US 10,774,329 B2
(45) Date of Patent: Sep. 15, 2020

(54) SYSTEM FOR THE BIOCONTROL OF PATHOGENS IN AQUACULTURE AND OTHER ANIMAL SYSTEMS

(71) Applicant: Pebble Labs USA Inc., Los Alamos, NM (US)

(72) Inventors: Richard T. Sayre, Los Alamos, NM (US); Tatiana Vinogradova-Shah, Los Alamos, NM (US)

(73) Assignee: PEBBLE LABS USA INC., Los Alamos, NM (US)

( * ) Notice: Subject to any disclaimer, the term of this patent is extended or adjusted under 35 U.S.C. 154(b) by 0 days.

(21) Appl. No.: 16/588,498

(22) Filed: Sep. 30, 2019

(65) Prior Publication Data

US 2020/0032267 A1 Jan. 30, 2020

Related U.S. Application Data

(63) Continuation-in-part of application No. PCT/US2018/025766, filed on Apr. 2, 2018.

(60) Provisional application No. 62/480,138, filed on Mar. 31, 2017.

(51) Int. Cl.
| | | |
|---|---|---|
| *C07H 21/04* | (2006.01) | |
| *C12N 15/113* | (2010.01) | |
| *A23K 50/80* | (2016.01) | |
| *A23K 10/18* | (2016.01) | |
| *C07K 16/08* | (2006.01) | |
| *C12N 15/11* | (2006.01) | |

(52) U.S. Cl.
CPC .......... *C12N 15/1131* (2013.01); *A23K 10/18* (2016.05); *A23K 50/80* (2016.05); *C07K 16/081* (2013.01); *C12N 15/111* (2013.01); *C12N 2310/11* (2013.01)

(58) Field of Classification Search
None
See application file for complete search history.

(56) References Cited

U.S. PATENT DOCUMENTS

| | | |
|---|---|---|
| 7,550,647 B2 | 6/2009 | Barratt et al. |
| 7,888,325 B2 | 2/2011 | Li et al. |
| 8,633,028 B2 | 1/2014 | Gross et al. |
| 8,828,961 B2 | 9/2014 | Loy et al. |
| 9,650,634 B2 | 5/2017 | Loy et al. |
| 10,004,797 B2 | 6/2018 | Harris et al. |
| 2005/0158326 A1 | 7/2005 | Chen et al. |
| 2008/0194504 A1 | 8/2008 | Kyle et al. |
| 2010/0092428 A1 | 4/2010 | Schmidt et al. |
| 2014/0371295 A1 | 12/2014 | Loy et al. |

OTHER PUBLICATIONS

International Search Report dated Aug. 10, 2018 in PCT Application No. PCT/US18/25766, filed on Apr. 2, 2018, 7 pages.
Sanchez-Martinez, et al., "White Sppot Syndrome Virus in cultured shrimp: A review", Aquaculture Research, 2007, 16 pp. 1339-1354.
Yadav, et al., "The Small Molecule DAM Inhibitor, Pyrimidinedione, Disrupts *Streptococcus pneumoniae* Biofilm Growth In Vitro", PLOS One, Oct. 2, 2015, pp. 1-35.
Walker, et al., "Emerging viral diseases of fish and shrimp", Vet. Res., 2010, EDP Sciences, pp. 1-24.
Soonthornchai, et al., "Interaction of *Vibrio* spp. with the Inner Surface of the Digestive Tract of Penaeus Tionodon", PLOS One, Aug. 18, 2015, pp. 1-18.
Taga, et al., "The LuxS-dependent autoinducer AI-2 controls the expression of an ABC transporter that functions in AI-2 uptake in *Salmonella typhimurium*", Molecular Microbiology, 2001, 17 pp. 777-793.
Thammasorn, et al., "Probiotic bacteria (Lactobacillus plantarum) expressing specific double-stranded RNA and its potential for controlling shrimp viral and bacterial diseases", Aquacult Int, Apr. 6, 2017, 14 pp. 1679-1692.
Mei, et al., "AidH, an Alpha/Beta-Hydrolase Fold Family Member from an *Ochrobactrum* sp. Strain, Is a Novel N-Acylhomoserine Lactonase", American Society for Microbiology, Aug. 2010, 10 pp. 4933-4942.
Sanjuktha, et al., "Comparative efficacy of double-standard RNAs targeting WSSV structural and nonstructural genes in controlling viral multiplication in Penaeus monodon", Research Gate, Feb. 21, 2012, 7 pp. 993-998.
Nakashima, et al., "Paired termini stabilize antisense RNAs and enhance conditional gene silencing in *Escherichia coli*", Nucleic Acids Research, Oct. 24, 2006, 10 pages.
Nguyen, et al., "RNA interference in shrimp and potential applications inaquaculture", Reviews in Aquaculture, 2016, 12 pp. 573-584.
O'Toole, "Microtiter Dish Biofilm Formation Assay", Journal of Visualized Experiments, 2011, 2 pages.
Flegel, et al., "Presence of multiple viruses in non-diseased, cultivated shrimp at harvest", Science Direct, 2004, 14 pp. 55-68.
Rajamani, et al., "N-Acyl Homoserine Lactone Lactonase, AiiA, Inactivation of Quorum-Sensing Agonists Produced by Chlamydomonas Reinhardtii (Chlorophyta) and Characterization of aiiA Transgenic Algae", Phycological Society of America, 2011, 9 p. 1219-1227.
Ruwandeepika, et al., "Expression and Quorum Sensing Regulation of Type III Secretion System Genes of Vibrio harveyi during Infection of Gnotobiotic Brine Shrimp", PLOS One, Dec. 4, 2015, 11 pages.
Julio, et al., "DNA Adenine Methylase Is Essential for Viability and Plays a Role in the Pathogenesis of Yersinia Dseudotuberculosis and Vibrio cholerae", American Society for Microbiology, Dec. 2001, 6 pp. 7610-7615.

(Continued)

*Primary Examiner* — Kimberly Chong
(74) *Attorney, Agent, or Firm* — Berg Hill Greenleaf Ruscitti LLP

(57) ABSTRACT

The inventive technology relates to novel paratransgenic strategies for the biocontrol of pathogens in animal systems using interfering RNA molecules expressed in genetically modified bacteria that may be configured to colonize a target host. In one preferred embodiment, the invention includes novel paratransgenic strategies for the biocontrol of pathogens in aquatic organisms raised in aquaculture environments.

17 Claims, 7 Drawing Sheets
Specification includes a Sequence Listing.

(56) References Cited

OTHER PUBLICATIONS

Hoa, et al., "Genotypic Variations in Tandem Repeat DNA Segments between Ribonucleotide Reductase Subunit Genes of White Spot Syndrome Virus (WSSV) Isolates from Vietnam", Diseases in Asian Aquaculture V, Jan. 2005, 13 pp. 339-351.
Krachler, et al., "Outer membrane adhesion factor multivalent adhesion molecule 7 initiates host cell binding during infection by Gram-negative pathogens", PNAS, Jul. 12, 2011, 6 pp. 11614-11619.
Defoirdt, et al., "Quorum sensing and quorum quenching in Vibrio harveyi: lessons learned from in vivo work", The ISME Journal, 2008, 8 pp. 19-26.
Collier, et al., "A DNA methylation ratchet governs progression through a bacterial cell cycle", PNAS, Oct. 23, 2007, 6 pp. 17111-17116.
Schryver, et al., "Early Mortality Syndrome Outbreaks: A Microbial Management Issue in Shrimp Farming?", PLOS, Apr. 2014, 2 pages.
Dunn, et al., "A vector for promoter trapping in Bacillus cereus", Gene, 1998, 9 pp. 297-305.
Durand, et al., "Quantitative real time PCR for the measurement of white spot syndrome virus in shrimp", Journal of Fish Diseases, 2002, 9 pp. 381-389.
Ma, et al., "Effects of antibacterials use in aquaculture on biogeochemical processes in marine sediment", Science Direct, 2005, 5 pp. 273-277.
Val, et al., "Fuse or die: how to survive the loss of Darn in Vibrio cholerae", Molecular Microbiolgy, Jan. 7, 2014, 14 pp. 665-678.
Berenstein, et al., "Genetic Organization of the Vibrio harveyi dnaA Gene Region and Analysis of the Function of the V. harveyi DnaA Protein in *Escherichia coli*", Journal of Bacteriology, May 2002, 6 pp. 2533-2538.
Lee, et al., "The opportunistic marine pathogen Vibrio parahaemolyticus becomes virulent by acquiring a plasmid that expresses a deadly toxin", PNAS, Aug. 25, 2015, 6 pp. 10798-10803.
Lezzerini, et al., "Specific RNA Interference in Caenorhabditis elegans by Ingested dsRNA Expressed in Bacillus subtilis", PLOS One, Apr. 30, 2015, 15 pages.
Cruz, et al., "Use of Probiotics in Aquaculture", International Scholarly Research Network, 2012, 13 pages.

SEQUENCE LISTING

<160> NUMBER OF SEQ ID NOS: 10

<210> SEQ ID NO 1
<211> LENGTH: 627
<212> TYPE: DNA
<213> ORGANISM: Artificial Sequence
<220> FEATURE:
<223> OTHER INFORMATION: dsWsv477

<400> SEQUENCE: 1

```
atgtatatct tcgtcgaagg ttccccctc acagggaaga gttcatggat gtccaagttg      60
atagatacag gatcatgtgg aatgtctttc ctcaatttc ttcgtatgaa cacttctgac    120
tactacaact ggcctgccga aatcgggaca gaacatctcc agttaggttt cagagaaacc    180
agagtggtgg atggaatgtt tgaacctgtc ctaaagacct tgtcgactc gtggaagaaa    240 gagcaaggaa aagagagttt gaaggaatat ctggactaca acggccaagt catggagatc    300
tacatcgcag aatggttgag acaaaggcca ctagccttcc acgtgtttac ctatacagat    360
gaagctgtca agagtggatt cttgaacgag gaggatctag atatggatac tgcaaccaag    420
tggatggctg aaattattag agagaagagg ggcaatattc aagaaataaa agtgacccct    480
agagtagtct tcaatggcaa tggttgtagt gcatgtttct ctaacactaa gagaaacttg    540
tataactttg aacaaacta taacaatgtt gtacattgtg atttgttgtg cccttttgca    600
aggcatagga ttgtacattt cttataa                                          627
```

<210> SEQ ID NO 2
<211> LENGTH: 601
<212> TYPE: DNA
<213> ORGANISM: Artificial Sequence
<220> FEATURE:
<223> OTHER INFORMATION: dsVp28

<400> SEQUENCE: 2

```
tcactctttc ggtcgtgtcg gccatcctcg ccatcactgc tgtgattgct gtatttattg      60 tgattttag gtatcacaac actgtgacca agaccatcga aacccacaca ggcaatatcg    120
agacaaacat ggatgaaaac ctccgcattc ctgtgactgc tgaggttgga tcaggctact    180
tcaagatgac tgatgtgtcc tttgacagcg acaccttggg caaaatcaag atccgcaatg    240
gaaagtctga tgcacagatg aaggaagaag atgcggatct tgtatcactc ccgtggaggg    300
ccgagcactc gaagtgactg tggggcggaa tctcaccttt gagggacat tcaaggtgtg    360 gaacaacaca tcaagaaaga tcaacatcac tggtatgcag atggtgccaa agattaaccc    420
atcaaaggcc tttgtcggta gctccaacac ctcctccttc accccgtct ctattgatga    480
```

```
ggatgaagtt ggcacctttg tgtgtggtac cacctttggc gcaccaattg cagctaccgc    540
cggtggaaat ctttttcgaca tgtacgtgca cgtcacctac tctggcactg agaccgagta   600
a                                                                    601
```

```
<210> SEQ ID NO 3
<211> LENGTH: 350
<212> TYPE: DNA
<213> ORGANISM: Artificial Sequence
<220> FEATURE:
<223> OTHER INFORMATION: dsVp19

<400> SEQUENCE: 3
gccaccacga ctaacactct cctttcggc aggaccggag cccaggccgc tggcccttct      60
tacaccatgg aagatcttga aggctccatg tctatggctc gcatgggtct cttttttgatc   120 gttgctatct caattggtat cctcgtcctg ccgtcatga atgtatggat gggaccaaag     180
aaggacagcg attctgacac tgataaggac accgatgatg atgacgacac tgccaacgat    240
aacgatgatg aggacaaata taagaacagg accaggata tgatgcttct ggctgggtcc     300
gctcttctgt tcctcgtttc cgccgccacc gttttatgt cttaccccaa                350
```

```
<210> SEQ ID NO 4
<211> LENGTH: 561
<212> TYPE: DNA
<213> ORGANISM: Artificial Sequence
<220> FEATURE:
<223> OTHER INFORMATION: dsLUC

<400> SEQUENCE: 4
acagcctggg catcagcaag cccaccatcg tgttcagcag caagaagggc ctggacaaag     60
tcatcaccgt gcagaaaacc gtgaccacca tcaagaccat cgtgatcctg acagcaagg    120 tggactaccg gggctaccag tgcctggaca ccttcatcaa gcggaacacc cccctggct    180 tccaggccag cagcttcaag accgtggagg tggaccggaa agaacaggtg ccctgatca    240 tgaacagcag cggcagcacc ggcctgccca agggcgtgca gctgacccac gagaacaccg   300
tgacccggtt cagccacgcc agggacccca tctacggcaa ccaggtgtcc cccggcaccg    360
ccgtgctgac cgtggtgccc ttccaccacg gcttcggcat gttcaccacc ctgggctacc    420
tgatctgcgg cttccgggtg gtgatgctga ccaagttcga cgaggaaacc ttcctgaaaa    480
ccctgcagga ctacaagtgc acctacgtga ttctggtgcc cacccctgttc gccatcctga   540 acaagagcga gctgctgaac a                                              561
```

```
<210> SEQ ID NO 5
<211> LENGTH: 121
<212> TYPE: PRT
<213> ORGANISM: White spot syndrome virus

<400> SEQUENCE: 5

Met Ala Thr Thr Thr Asn Thr Leu Pro Phe Gly Arg Thr Gly Ala Gln
1               5                   10                  15

Ala Ala Gly Pro Ser Tyr Thr Met Glu Asp Leu Glu Gly Ser Met Ser
            20                  25                  30

Met Ala Arg Met Gly Leu Phe Leu Ile Val Ala Ile Ser Ile Gly Ile
        35                  40                  45

Leu Val Leu Ala Val Met Asn Val Trp Met Gly Pro Lys Lys Asp Ser
    50                  55                  60

Asp Ser Asp Thr Asp Lys Asp Thr Asp Asp Asp Asp Thr Ala Asn
```

```
                65                    70                   75                   80
Asp Asn Asp Asp Glu Asp Lys Tyr Lys Asn Arg Thr Arg Asp Met Met
                        85                   90                   95

Leu Leu Ala Gly Ser Ala Leu Leu Phe Leu Val Ser Ala Ala Thr Val
                100                  105                  110

Phe Met Ser Tyr Pro Lys Arg Arg Gln
                115                  120

<210> SEQ ID NO 6
<211> LENGTH: 366
<212> TYPE: DNA
<213> ORGANISM: White spot syndrome virus

<400> SEQUENCE: 6
atggccacca cgactaacac tcttcctttc ggcaggaccg gagcccaggc cgctggccct        60
tcttacacca tggaagatct tgaaggctcc atgtctatgg ctcgcatggg tctcttttg       120 atcgttgcta tctcaattgg tatcctcgtc ctggccgtca tgaatgtatg gatgggacca      180
aagaaggaca gcgattctga cactgataag gacaccgatg atgatgacga cactgccaac      240
gataacgatg atgaggacaa atataagaac aggaccaggg atatgatgct tctggctggg      300
tccgctcttc tgttcctcgt ttccgccgcc accgttttta tgtcttaccc caagaggagg      360
cagtaa                                                                 366

<210> SEQ ID NO 7
<211> LENGTH: 172
<212> TYPE: PRT
<213> ORGANISM: White spot syndrome virus

<400> SEQUENCE: 7

Val Thr Lys Thr Ile Glu Thr His Thr Asp Asn Ile Glu Thr Asn Met
  1               5                   10                  15

Asp Glu Asn Leu Arg Ile Pro Val Thr Ala Glu Val Gly Ser Gly Tyr
                 20                   25                  30

Phe Lys Met Thr Asp Val Ser Phe Asp Ser Asp Thr Leu Gly Lys Ile
             35                   40                  45

Lys Ile Arg Asn Gly Lys Ser Asp Ala Gln Met Lys Glu Glu Asp Ala
     50                   55                  60

Asp Leu Val Ile Thr Pro Val Glu Gly Arg Ala Leu Glu Val Thr Val
 65                   70                  75                  80

Gly Gln Asn Leu Thr Phe Glu Gly Thr Phe Lys Val Trp Asn Asn Thr
                 85                  90                   95

Ser Arg Lys Ile Asn Ile Thr Gly Met Gln Met Val Pro Lys Ile Asn
                100                 105                  110

Pro Ser Lys Ala Phe Val Gly Ser Ser Asn Thr Ser Ser Phe Thr Pro
            115                 120                  125

Val Ser Ile Asp Glu Asp Glu Val Gly Thr Phe Val Cys Gly Thr Thr
        130                 135                  140

Phe Gly Ala Pro Ile Ala Ala Thr Ala Gly Gly Asn Leu Phe Asp Met
145                 150                  155                  160

Tyr Val His Val Thr Tyr Ser Gly Thr Glu Thr Glu
                165                  170

<210> SEQ ID NO 8
<211> LENGTH: 516
<212> TYPE: DNA
<213> ORGANISM: White spot syndrome virus
```

<400> SEQUENCE: 8
gtgaccaaga ccatcgaaac ccacacagac aatatcgaga caaacatgga tgaaaacctc 60
cgcattcctg tgactgctga ggttggatca ggctacttca agatgactga tgtgtccttt 120
gacagcgaca ccttgggcaa aatcaagatc cgcaatggaa agtctgatgc acagatgaag 180
gaagaagatg cggatcttgt catcactccc gtggagggcc gagcactcga agtgactgtg 240
gggcagaatc tcacctttga gggaacattc aaggtgtgga acaacacatc aagaaagatc 300
aacatcactg gtatgcagat ggtgccaaag attaacccat caaaggcctt tgtcggtagc 360
tccaacacct cctccttcac ccccgtctct attgatgagg atgaagttgg cacctttgtg 420
tgtggtacca cctttggcgc accaattgca gctaccgccg gtggaaatct tttcgacatg 480
tacgtgcacg tcacctactc tggcactgag accgag 516

<210> SEQ ID NO 9
<211> LENGTH: 208
<212> TYPE: PRT
<213> ORGANISM: White spot syndrome virus

<400> SEQUENCE: 9

Met Tyr Ile Phe Val Glu Gly Ser Pro Leu Thr Gly Lys Ser Ser Trp
1 5 10 15

Met Ser Lys Leu Ile Asp Thr Gly Ser Cys Gly Met Ser Phe Leu Asn
20 25 30

Phe Leu Arg Met Asn Thr Ser Asp Tyr Tyr Asn Trp Pro Ala Glu Ile
35 40 45

Gly Thr Glu His Leu Gln Leu Gly Phe Arg Glu Thr Arg Val Val Asp
50 55 60

Gly Met Phe Glu Pro Val Leu Lys Thr Phe Val Asp Ser Trp Lys Lys
65 70 75 80

Glu Gln Gly Lys Glu Ser Leu Lys Glu Tyr Leu Asp Tyr Asn Gly Gln
85 90 95

Val Met Glu Ile Tyr Ile Ala Glu Trp Leu Arg Gln Arg Pro Leu Ala
100 105 110

Phe His Val Phe Thr Tyr Thr Asp Glu Ala Val Lys Ser Gly Phe Leu
115 120 125

Asn Glu Glu Asp Leu Asp Met Asp Thr Ala Thr Lys Trp Met Ala Glu
130 135 140

Ile Ile Arg Glu Lys Arg Gly Asn Ile Gln Glu Ile Lys Val Thr Pro
145 150 155 160

Arg Val Val Phe Asn Gly Asn Gly Cys Ser Ala Cys Phe Ser Asn Thr
165 170 175

Lys Arg Asn Leu Tyr Asn Phe Gly Thr Asn Tyr Asn Asn Val Val His
180 185 190

Cys Asp Leu Leu Cys Pro Phe Ala Arg His Arg Ile Val His Phe Leu
195 200 205

<210> SEQ ID NO 10
<211> LENGTH: 627
<212> TYPE: DNA
<213> ORGANISM: White spot syndrome virus

<400> SEQUENCE: 10
atgtatatct tcgtcgaagg ttcccccctc acagggaaga gttcatggat gtccaagttg 60
atagatacag gatcatgtgg aatgtctttc ctcaattttc ttcgtatgaa cacttctgac 120

-continued

```
tactacaact ggcctgccga aatcgggaca gaacatctcc agttaggttt cagagaaacc      180
agagtggtgg atggaatgtt tgaacctgtc ctaaagacct ttgtcgactc gtggaagaaa      240
gagcaaggaa aagagagttt gaaggaatat ctggactaca acggccaagt catggagatc      300
tacatcgcag aatggttgag acaaaggcca ctagccttcc acgtgtttac ctatacagat      360
gaagctgtca agagtggatt cttgaacgag gaggatctag atatggatac tgcaaccaag      420
tggatggctg aaattattag agagaagagg ggcaatattc aagaaataaa agtgacccct      480
agagtagtct tcaatggcaa tggttgtagt gcatgtttct ctaacactaa gagaaacttg      540
tataactttg gaacaaacta taacaatgtt gtacattgtg atttgttgtg ccctttttgca     600 aggcatagga ttgtacattt cttataa                                         627
```

SYSTEM FOR THE BIOCONTROL OF PATHOGENS IN AQUACULTURE AND OTHER ANIMAL SYSTEMS

CROSS REFERENCE TO RELATED APPLICATIONS

This application is a Continuation-in-Part of International Application No. PCT/US18/25766, filed Apr. 2, 2018; which claims the benefit of and priority to U.S. Provisional Application No. 62/480,138, filed Mar. 31, 2017. The entire specifications and figures of the above-referenced applications are hereby incorporated, in their entirety by reference.

SEQUENCE LISTING

The instant application contains a Sequence Listing which has been submitted electronically in ASCII format and is hereby incorporated by reference in its entirety.

TECHNICAL FIELD

Generally, the inventive technology relates to novel strategies for disease control in animal systems. Specifically, the inventive technology relates to novel methods, systems and compositions for the biocontrol of aquatic pathogens in aquatic systems. Specifically, the invention may comprise novel techniques, systems, and methods for the biocontrol of disease-transmitting pathogens affecting shrimp in aquaculture systems.

BACKGROUND

The development of aquaculture has generated a significant shift in global food production away from traditional catch production methods. Driven primarily by population increases, as well as a lack of growth in traditional capture fishery production, aquaculture has expanded rapidly to become a major component in the world-wide food production eco-system. Aquaculture is now seen as playing a key role in many emerging economies, by virtue of its potential to contribute to increased food production while helping reduce pressure on fish resources. As noted by the United Nations Food and Agriculture Organization (UNFAO) in its 2016 Report on the State of the World Fisheries and Aquaculture, aquaculture is the fastest growing area of animal protein production and has significantly outpaced traditional capture fishery production. For example, the UNFAO estimates that aquaculture production now accounts for half of all seafood produced for human consumption.

The increasing global population, growing demand for seafood, and limitations on production from capture fisheries will inevitably lead the continued global expansion of aquaculture with its associated risks of disease emergence and spread. Despite the world's growing reliance on aquaculture as a primary source of food production, especially in many developing economies, traditional aquaculture systems present several technical and biological challenges that limit their overall effectiveness.

One major drawback of aquaculture systems is that the aquatic animals are typically placed in high density production systems. This can result in stress from crowding and sub-optimal water quality conditions that provide for easy transmission of disease. In particular, disease outbreaks in aquaculture systems can result in massive losses among aquatic populations, resulting in large economic losses in commercial aquaculture. Indeed, such disease outbreaks have reportedly cost the aquaculture industry tens of billions dollars in the last 20 years.

In the case of shrimp aquaculture, the problem of disease is especially severe. According to the UNFAO, although global aquaculture shrimp production has increased, major producing countries, particularly in Asia, have experienced a significant decline in output as a result of widespread shrimp disease. There are several reasons for this.

First, unlike vertebrates, shrimp lack many of the key components of adaptive and innate immune response mechanisms preventing many traditional methods of inducing or enhancing natural disease resistance.

Second, most of the major pathogenic viruses cause very low level persistent infections that can occur at moderate to very high prevalence in apparently healthy shrimp populations. The majority of shrimp pathogens are transmitted vertically and disease is the result of a massive viral amplification that follows exposure to various forms of environmental or physiological stress. Stressors can include handling, spawning, poor water quality, or abrupt changes in temperature or salinity. Shrimp viruses can also be transmitted horizontally. Once viral loads are high and disease is manifest, horizontal transmission of infection is accompanied by transmission of disease.

Third, shrimp commonly are infected simultaneously or sequentially with multiple viruses, or even different strains of the same virus. This fact poses significant challenges for diagnosis, detection, and pathogen exclusion in aquaculture systems.

As one example among many, white spot syndrome (WSS) is a viral disease caused by white spot syndrome virus (WSSV). WSSV is a major pathogen in shrimp that causes high mortality and huge economic losses in shrimp aquaculture. The WSS virion is a nonoccluded ellipsoid- or bacilliform-shaped enveloped particle about 275 nm in length and 120 nm in width. Its circular double-stranded DNA consists of 300 kbp covering approximately 185 open reading frames (ORFs). WSSV is currently one of the most significant impediments to the economical sustainability and growth of the global crustacean aquaculture trade. It has caused the loss of billions in USD since its original outbreaks in the early 1990s. To date, WSSV outbreaks have been detected in most major shrimp producing areas including Asia, Central, South and North America, Europe and Africa.

Traditional efforts to prevent and treat shrimp pathogens, such as WSSV, have been met with limited success. For example, attempts to reduce environmental and physiological stressors has been limited due to the economic production needs of aquaculture systems as well as a lack of technical expertise and appropriate aquaculture facilities in many developing countries. Other attempts have been made to create and isolate pathogen-free populations for aquaculture.

However, such efforts are slow and require significant expertise and diagnostic capabilities that are prohibitively expensive. Large-scale applications of antibiotics have been applied to shrimp aquaculture, in particular during the production cycle, both in the larval and growth phases. However, the use of antibiotics in aquaculture has been associated with environmental and human health problems, including bacterial resistance, and persistence of the disease in the aquatic environment. The accumulation of antibiotic residues in the edible tissues of shrimp may also alter human intestinal flora and cause food poisoning or allergy problems. Most importantly, antibiotics are ineffective against viruses. Other methods such as the application of immunostimulants or bacteriophage treatments to target specific pathogens have been tried with limited commercial and practical success.

An effective system for the biocontrol of pathogens in aquaculture and other animal systems may be: 1) pathogen (virus)-specific so as to not kill off-target organisms; 2) robust or catalytic in mode of action; 3) stable and not easily lost throughout development of the target animal; 4) efficient to deliver; 5) simple to manage and low cost; and 6) self-sustainable or regenerating.

To that end, methods of regulating gene expression in pathogens may be an avenue to address the concerns addressed above. Regulating gene expression either by increasing expression or decreasing expression of genes responsible for virulence is considered beneficial for treatment of diseases. This is especially important in those diseases in which master regulatory genes have been identified. While a majority of efforts have been extended toward enhancing gene expression, down-regulating specific gene expression is equally important. A naturally occurring gene-silencing mechanism triggered by double-stranded RNA (dsRNA), designated as small interfering RNA (siRNA), has emerged as a very important tool to suppress or knock down gene expression in many systems. RNA interference is triggered by dsRNA that is cleaved by an RNase-III-like enzyme, Dicer, into 21-25 nucleotide fragments with characteristic 5' and 3' termini. These siRNAs act as guides for a multiprotein complex, including a PAZ/PIWI domain containing the protein Argonaute2, that cleaves the target mRNA. These gene-silencing mechanisms are highly specific and potent and can potentially induce inhibition of gene expression throughout an organism.

The last two decades have also seen tremendous progress in gene expression technology, including the continued development of both non-viral and viral vectors. The non-viral approach to gene expression involves the use of plasmid DNAs (pDNAs), which have a number of advantages, including ease of use and preparation, stability and heat resistance, and unlimited size. The plasmids do not replicate in mammalian hosts and do not integrate into host genomes, yet they can persist in host cells and express the cloned gene for a period of weeks to months.

One area that has seen renewed interest in the use of inhibitory RNA molecules is infectious diseases, and in particular, pathogens that affect aquaculture populations. Such strategies for the biocontrol of pathogens may include paratransgenesis and/or the application of paratransgenic principles. Paratransgenesis generally refers to systems whereby symbiotic bacteria, or bacteria capable of colonizing the host for a sufficient amount of time to delivery a therapeutic molecule such as a dsRNA, are genetically modified and reintroduced in the pathogen-bearing host or a pathogen-susceptible population, such as shrimp in aquaculture, where they express effector molecules. However, paratransgenesis has several technical limitations. For example, bacteria to be used in paratransgenesis must generally have three key components: an effector molecule that achieves the desired effect; a mechanism to display or excrete the effector molecule; and bacteria that can survive in the host long enough to produce the expected amount of effector molecules and thereby achieve the desired effect in the host. Therefore, finding such suitable bacteria that fit all of these criteria is very difficult.

Paratransgenesis is generally understood as a technique that attempts to eliminate a pathogen from vector populations through transgenesis of a symbiont of the vector. The goal of this technique is to control vector-borne diseases. The first step is to identify proteins that prevent the vector species from transmitting the pathogen. The genes coding for these proteins are then introduced into the symbiont, so that they can be expressed in the vector. The final step in the strategy is to introduce these transgenic symbionts into vector populations in the wild. Characteristics of a successful n order to perform paratransgenesis may include:

The symbiotic bacteria can be grown in vitro easily.
They can be genetically modified, such as through transformation with a plasmid containing the desired gene.
The engineered symbiont is stable and safe.
The association between vector and symbiont cannot be attenuated.
Field delivery is easily handled.

A paratransgenic system is a system that can achieve paratransgenesis in a target organism. Identification of suitable commensal bacteria that are non-pathogenic to humans or animals among the many organisms that a host may harbor, particularly in their digestive systems, is paramount for the success of a paratransgenic system. For example, the chosen bacteria should be capable of colonizing a wide variety of shrimp species so that they can be deployed in different species and isolated strains.

Furthermore, a well-designed paratransgenic system must also ensure that the effector molecule does not interfere with any critical host process, such as reproduction and the like. Such technical and physiological challenges make the development of paratransgenic systems extremely difficult. Importantly, these technical issues are such that many paratransgenic systems are neither effective nor appropriate as an effective biocontrol strategy, especially in complex organisms like shrimp. These difficulties may also prevent many paratransgenic systems from being appropriately scaled-up to be effective for environmental deployment. Generally, biocontrol means utilizing disease-suppressive microorganisms to eliminate, control or prevent infection, expression and/or transmission of selected pathogens.

The foregoing problems regarding the biocontrol of pathogens in aquaculture and other animal systems may represent a long-felt need for an effective—and economical—solution to the same. While implementing elements may have been available, actual attempts to meet this need may have been lacking to some degree. This may have been due to a failure of those having ordinary skill in the art to fully appreciate or understand the nature of the problems and challenges involved. As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field.

As will be discussed in more detail below, the current inventive technology overcomes the limitations of traditional pathogen control systems, while meeting the objectives of a truly effective vector biocontrol strategy.

SUMMARY OF THE INVENTION(S)

One aim of the present invention may include novel paratransgenic biocontrol strategies. In this embodiment, the inventive technology includes various cross-kingdom mechanisms for the knockdown of essential viral genes. This may be accomplished through the introduction of engineered microorganisms into host populations that express specific inhibitory RNA molecules that may downregulate and/or suppress selected viral and/or host genes.

Another aim of the present invention may include novel paratransgenic biocontrol strategies for aquaculture populations. In this embodiment, the inventive technology includes various cross-kingdom mechanisms for the knockdown of essential viral genes in aquatic animals grown in aquaculture systems. This may be accomplished through the introduction of engineered microorganisms into aquaculture animal populations that express specific inhibitory RNA molecules that may downregulate and/or suppress selected viral and/or host genes.

Another specific aim of the invention may provide a novel paratransgenic system that may suppress expression and propagation of the WSSV, among other viral pathogens, in shrimp aquaculture populations. This system may include the introduction of a genetically-modified bacteria transformed to express select dsRNAs that may target and suppress one or more pathogen virus genes. Such targets may include, but not be limited to, the generally conserved region of the WSSV genome coding for: viral capsid protein 19 (vp19), and/or viral capsid protein 19 gene (vp28) and/or early non-structural gene 477 (Wsv477).

Another aim of the invention may include methods of targeting multiple essential virus-specific gene targets for silencing, such that it may be possible to selectively diminish viral pathogens in adult shrimp populations grown in aquaculture environments. In this embodiment, the invention may include the generation of feeds containing genetically modified bacteria configured to express select dsRNAs that may target and suppress one or more pathogen virus genes. In one embodiment, such a treated feed may be introduced to a pathogen-susceptible or pathogen-affected population. In such an embodiment, feeds containing genetically modified bacteria configured to express select dsRNAs that may target and suppress one or more WSSV genes may be introduced to WSSV-susceptible or WSSV-affected shrimp aquaculture populations. As siRNAs may be catalytic in activity, their potential effectiveness and safety may well be greater that traditional viral control methods currently employed within the aquaculture industry. In addition, in certain embodiments the inhibitory RNAs are non-immunogenic, such that they can be designed to be species specific so that non-target organisms are not harmed and/or affected. Finally, since a bacterial-based dsRNA delivery system may be self-sustaining and long-lasting, many fewer feed applications may be needed. In some cases, a single feeding may only be needed.

In some cases, such interfering RNA molecules, such as dsRNA, may act as a vaccine immunizing individual animals. As such, one aim of the invention may include the use of genetically modified bacteria to colonize and express dsRNA molecules that provided individual or herd immunity in aquatic animals, such as shrimp populations grown in aquaculture systems.

Another aim of the invention may be the generation of genetically modified symbiotic and/or probiotic bacterial strain that may express one or more inhibitory RNA molecules. In a certain embodiment, a shrimp probiotic bacteria such as Bacillus subtilis, may be genetically modified to express one or more inhibitory RNA molecules directed to essential WSSV genes.

Another aim of the invention present inventive technology may include systems and methods for introducing inhibitory RNA molecules into a target host through infection by genetically engineered microorganisms. In one embodiment, the invention may provide for genetically engineered microorganisms that may express one or more inhibitory RNA molecules within a target organism. Such target organisms may include aquatic animals, aquatic animals in aquaculture systems as well as other vertebrate and invertebrate animals generally.

Another aim of the invention may include methods and compositions for the creation of inhibitory RNA molecules, such as dsRNA, may initiate biological processes that may inhibit or knock-down essential gene expression, typically by causing the destruction of specific mRNA molecules within the cell in multiple animal systems. Additional embodiments may introduce inhibitory RNA molecules into a target organism that inhibit genes necessary for pathogen virulence in multiple animal systems. Such embodiments may include introduction of inhibitory RNA molecules into target organisms that may target virulence genes, viral coat proteins, fungal cell wall genes, pathogenic component genes, species-specific metabolic genes and the like.

Additional aims of the invention may include improved delivery systems for inhibitory RNA molecules, for example through the use of stabilizing factors, such as stabilizing proteins and the like. Another preferred embodiment of the inventive technology may include improved systems to facilitate the transmission of inhibitory RNA molecules within the target organism. Yet further embodiments may include genetically modified microorganisms that may include genetic constructs that may further co-express certain proteins having processing enzymatic activity. Such co-expressed proteins may include enzymes that may inhibit and/or enhance post-translational processing and/or modification of inhibitory RNA molecules. Other similar embodiments may include the introduction of microorganisms into a target organism that may express, or even over-express, various genes that may enhance mobilization of inhibitory RNA molecules and/or genes that may activate secondary downstream host genes that may target pathogenic pathways.

Finally, the present inventors describe embodiments of the invention including protocol for shrimp feeding by a RNaseIII deficient *Bacillus subtilis* strain (BG322) expressing WSSV-specific dsRNA, and shrimp WSSV challenge experiments. The present inventors demonstrate, that in this embodiment, when given with feed including BG322, this genetically modified bacteria is able to survive and persist in shrimp intestines. The present inventors further demonstrated that the mortality count from WSSV challenge experiments for shrimp fed by bacteria expressing WSSV-targeting dsRNA compare to shrimp fed by bacteria expressing unspecific dsRNA indicates a 50% decrease in mortality for shrimp from first group. Additionally, the present inventors show 3-4 log reductions in viral replication in shrimp fed by WSSV-specific dsRNA. The present inventors further demonstrate that the presence of WSSV-specific fraction of siRNA in total RNA extracted from shrimp fed by WSSV-dsRNA, which siRNAs are absent in shrimp fed by unspecific dsRNA or shrimp not fed by any dsRNA. Taken together, in these embodiments, the present inventors demonstrate that delivery of virus-specific dsRNA by enteric intestine-colonizing bacteria is an efficient platform for immunizing and/or treating viral shrimp infections.

BRIEF DESCRIPTION OF THE FIGURES

The accompanying figures, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the figures.

MODE(S) FOR CARRYING OUT THE INVENTION(S)

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 6:
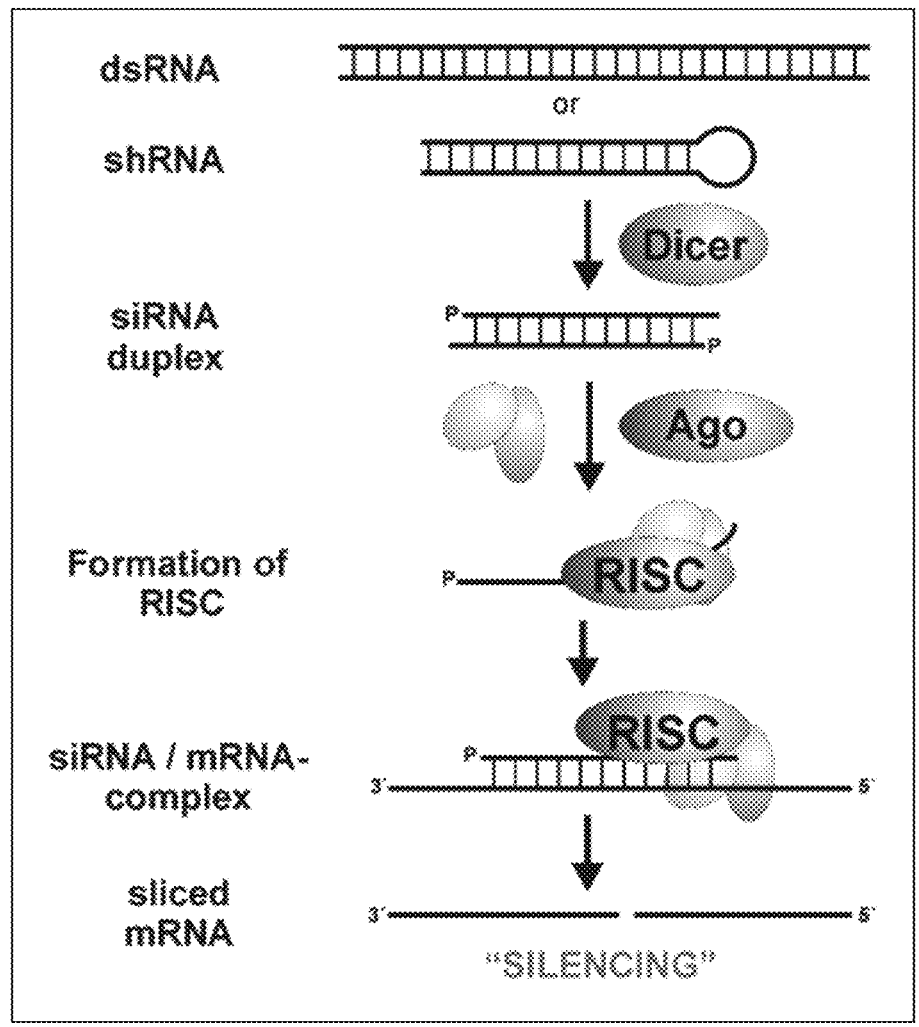
FIG. 6: Schematic for selective inactivation of target gene using dsRNA to initiate RNA interference response in a target host cell.

In one embodiment, the inventive technology may comprise systems, methods and compositions to control specific pathogens by selective inactivation of pathogenic, essential or other genes. This targeted gene inactivation may be accomplished by the expression and delivery of inhibitory RNA molecules, such as double stranded RNA (dsRNA) or small hairpin RNA (shRNA), to the target host cells where pathogen replication may occur. As generally shown in FIG. 6, in a target host, the dsRNA may be processed into small interfering RNAs (siRNAs) of ~approximately 21 nucleotides in length through the action of the enzyme, Dicer. These siRNAs may further interact with the Ago and RISC protein complexes to bind to the targeted pathogen-specific mRNA sequence. Finally, the RISC complex may cleave the pathogen-specific mRNA, silencing or knocking down the expression of the targeted pathogenic or other target gene and blocking pathogen virulence, replication and/or proliferation.

Additional embodiments may generally include gene inactivation of one, or a plurality of target genes. For example, in one preferred embodiment, gene inactivation may be directed to one or more pathogen genes that are essential to virulence, coat proteins, metabolic activity, infection pathways and/or energy-production and the like.

Delivery of the inhibitory RNA molecules to a target animal/cell/tissue may be accomplished through a trans-kingdom delivery system. In a preferred embodiment, the delivery of inhibitory RNA molecules may be accomplished through the introduction of genetically modified host-specific microorganisms, such as enteric or other bacteria. Since bacteria cannot process dsRNA to siRNA as they lack the Dicer/RISC machinery, dsRNA delivered to a target host must be processed by the host into siRNAs that may inactivate the targeted viral gene. Such genetically modified host-specific microorganisms may generally be referred to as probiotic bacteria or genetically modified bacteria, which may include: 1) microorganisms that are part of the target animals normal internal or external bacterial microbiome; 2) microorganisms that have been modified to be capable of colonizing a target animal, tissue, cell or host environment; 3) microorganisms that that are utilized as a food or energy source by the target host; or 4) microorganisms that have been modified to colonize a specific animal, tissue, cell or host environment. In a preferred embodiment, one or more enteric bacteria may be selected from the group: Acidimicrobiia; Actinobacteria; Alphaprotcobactcria; Anaerolineae; Bacilli; Bactcroidia; Betaproteobacteria; Clostridia; Deltaproteobacteria; Epsilonproteobacteria; Flavobacteria; Fusobactcria; Gammaproteobacteria; Mollicutes; Opitutac; Oscillatoriophycideae; Phycisphaerae; Planctomycetia; Rubrobactcria; Sphingobactcriia; Synechococcophycideae; Thermomicrohia; and Verrucomicrobiae.

The inventive technology may, in a preferred embodiment, include the trans-kingdom delivery of inhibitory RNA molecules, such as dsRNA, shRNA, siRNA and micro RNAs, for shrimp and other aquatic organisms. In one embodiment, the invention may comprise a dsRNA-mediated disease control system that may be configured to inactivate one or more viral gene targets in aquatic organisms such as shrimp. In one preferred embodiment, the invention may comprise a dsRNA-mediated disease control system that may be configured to inactivate one or more viral gene targets in aquatic organisms such as shrimp grown in aquaculture. Examples of shrimp-specific target pathogens may include, but not be limited to: white spot syndrome virus (WSSV); infectious hypodermal and hematopoietic necrosis virus (IHHNV); yellow head virus (YHV); Taura syndrome virus (TSV); and infectious myonecrosis virus (IMNV) and the like.

The inventive technology may also comprise a system for the trans-kingdom delivery of inhibitory RNA molecules to other aquatic vertebrates. In certain embodiments, examples of aquatic vertebrate pathogens may include, but not be limited, to those causing viral hemorrhagic septicemia, infectious pancreatic necrosis, viremia of carp, infectious hematopoietic necrosis virus, channel catfish virus, grass carp hemorrhagic virus, nodaviridae such as nervous necrosis virus or striped jack nervous necrosis virus, infectious salmon anaemia virus; and the parasites *Ceratomyxa shasta, Ichthyophthirius multifillius, Cryptobia salmositica, Lepeophtheirus salmonis*, Tetrahymena species, Trichodina species and Epistylus species, spring viraemia of carp (SVC) and Epizootic haematopoietic necrosis (EHNV) and the like.

Figure 7:
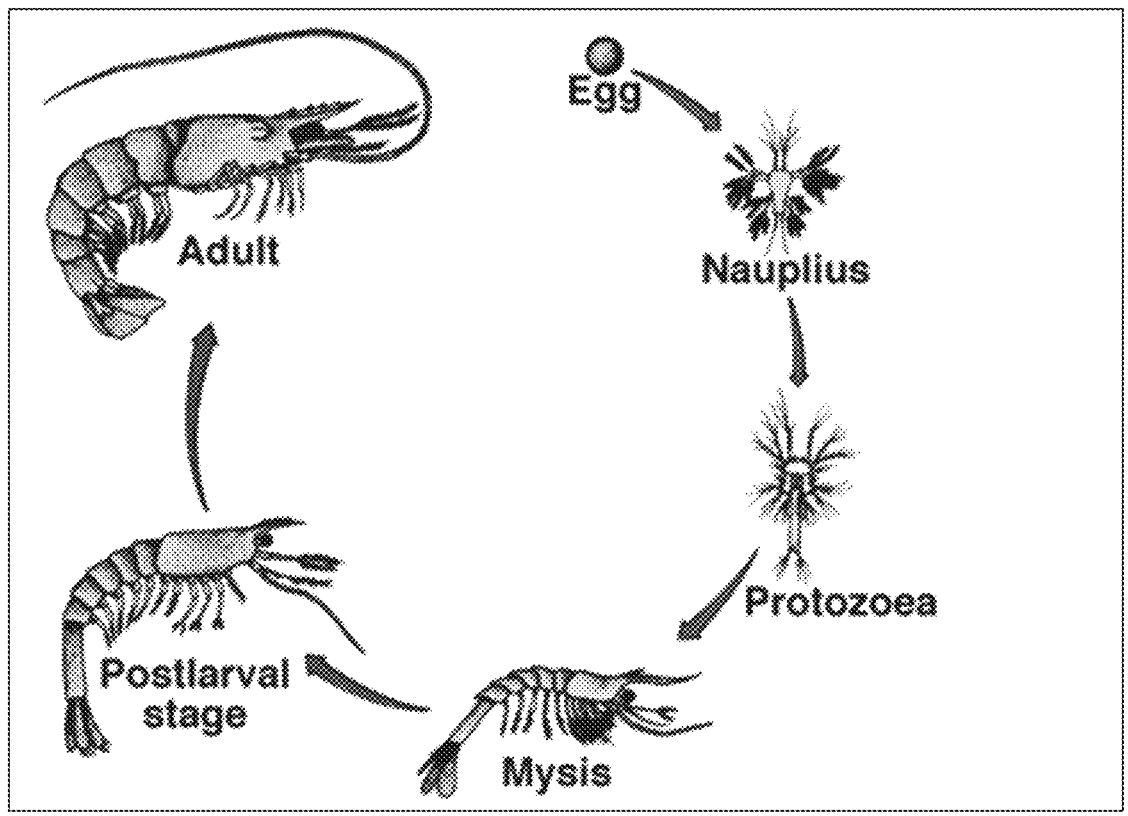
FIG. 7: Schematic for demonstrating typical life-cycle for shrimp.

As noted above, in a preferred embodiment, one or more inhibitory RNA molecules, in this instance dsRNA, may be delivered to a target host/population of shrimp through genetically modified enteric bacteria that may naturally, or be configured to, colonize in the gut of the shrimp. In this embodiment, once colonized in the host, vertical transmission of the modified bacteria may be passed to the host's progeny, thus naturally replicating the pathogenic resistance to subsequent generations. In certain embodiments, genetically modified bacteria expressing one or more inhibitory RNA molecules may colonize a shrimp throughout its lifecycle. For example, as generally shown in FIG. 7, genetically modified bacteria expressing one or more inhibitory RNA molecules may colonize a shrimp while it is: an egg, a nauplius, a protozoea, a mysis, paost-larval stage or an adult. In this embodiment, the colonized bacteria may express inhibitory RNA molecules, such as dsRNA/shRNAs, that may further be processed by the host's DICER/RISC complex allowing pathogen-specific mRNA silencing/inactivation of essential pathogen genes. Moreover, these colonized enteric bacteria, having permanently and/or temporarily become a part of the host's natural microbiome, may continuously deliver the dsRNA molecules via the intestine from the earliest larval stages to the adult stage, providing pathogen-specific mRNA silencing/inactivation of essential pathogen genes throughout the host's lifecycle. In addition, as the enteric bacteria vector may be an already naturally occurring part of the host's microbiome, its presence may not pose any risk to the organism, environment or end-consumers.

Additionally, in certain embodiments the modified bacteria may also be horizontally transmitted to a host population through the distribution of the modified bacteria in treated feed, or feed containing the genetically modified bacteria, or propagation of the genetically modified bacteria into the environment as excreted animal waste. Such a feature may allow for the one-time or at least only periodic administration of the modified bacteria to the host and/or host's environment generating a significant commercial advantage. The inventive technology may further comprise methods and techniques to control the levels and timing of the expression of inhibitory RNA molecules in the target organism.

In one preferred embodiment, the expression of one or more inhibitory RNA molecules may be under the control of a novel gene switch. This gene switch may be controlled by a switch molecule, which may be a water-soluble and food-grade molecule that can be added to a host organism's environment, such as an aquaculture pond or a food supply. The presence of this switch molecule may activate dsRNA production. In its absence, dsRNA production may not occur, or may only occur at negligible levels. In a preferred embodiment, aquaculture shrimp, or other target organisms may be infected with one or more viral targeting dsRNA-producing enteric bacteria while the timing and level of production of pathogen gene inactivating dsRNAs may be regulated by the novel gene switch.

The inventive technology may include methods and techniques for the generation of host-specific bacteria, and in particular, host-specific enteric bacteria that may act as an appropriate delivery vector for inhibitory RNA molecules. As an exemplary model, shrimp may be utilized as a target host. However, as can be appreciated by one of ordinary skill in the art, such methods and techniques may be applied to a variety of different organisms.

In this preferred embodiment, one or more shrimp gut samples from various larvae and adult shrimp species may be captured from the wild and characterized to identify the associated bacterial metagenome. From this initial genomic characterization, a list of target bacteria that inhabit the larval gut, as well as their species-specific relative abundance may be established. Additional steps in this characterization may include comparing and contrasting the metagenome of the enteric bacteria from adults metamorphosed from the aforementioned larvae to determine which bacterial species persist from larvae to adult stages and in what proportions.

In certain embodiments, a host-specific bacteria may include one or more of the following characteristics: 1) a dominant bacteria in the gut flora of both the larval and adult stages of shrimp; 2) culturable outside of the shrimp, for example in a fermenter; 3) no known adverse environmental or health impacts on non-target organisms; 4) capable of being genetically engineered to stably express and deliver dsRNA in sufficient quantities to inhibit target gene replication, in at least one, but preferably, all life stages of the shrimp.

Bacterial RNAse IIIs may degrade inhibitory RNA molecules such as dsRNA. As such, in one embodiment, the inventive technology may include modification of the previously identified host-specific bacteria, or probiotic, to have decreased RNase III expression, or inactivated RNase III function or activity. This decrease or inactivation in RNAase III expression and/or activity may inhibit or decrease RNase III-mediated processing of dsRNA into smaller RNA species. In one preferred embodiment, the previously identified host-specific bacteria may be genetically modified to efficiently express inhibitory RNA molecules in an RNAse III deficient background. In this preferred embodiment, the RNAse IIIs genes of the host-specific bacteria may be knocked out by homologous recombination or other appropriate methods.

Another embodiment of the inventive technology may include systems and methods to facilitate the overexpression of host-specific bacterial genes known to enhance stabilization and/or mobilization of inhibitory RNA molecules. In this preferred embodiment, one or more genes known to stabilize dsRNA may be overexpressed to enhance its lifetime and facilitate its movement within host organism/cell/tissue. In another preferred embodiment, one or more genes that regulate or suppress genes that are known to stabilize dsRNA may be knocked-out resulting in their upregulation thereby enhancing dsRNA's lifetime to facilitate its movement within host organisms to enhance the viral gene inhibition. Additional embodiments may also overexpress genes or target gene knockouts that may result in the upregulation of membrane vesicular trafficking to facilitate dsRNA mobilization and delivery to the host organism.

Each of the aforementioned systems may be embodied in genetic constructs that may include transcription regulation elements such as promoters, terminators, co-activators and co-repressors and other control elements as may be regulated in prokaryotic as well as eukaryotic systems. Such systems may allow for control of the type, timing and amount of, inhibitory RNA molecules or other proteins, expressed within the system. Additional embodiments may include genetic constructs that may be induced through additional outside and/or environmental factors, such as the presence of a specific protein or compound, such as stress related proteins generated in response to a pathogen or even proteins and other precursor compounds generated by pathogens and the like.

Additional optimization procedures of the current inventive technology may include introducing modified microorganisms into shrimp larvae in a laboratory environment using competition studies with multiple food targets and different densities of microorganisms expressing dsRNA, to determine the effective dosage for suppressing viral replication. Shrimp larval tissues may be analyzed by in situ RNA hybridization to the determine the cellular location where gene expression was most impacted by dsRNA to better select additional target genes for dsRNA-mediated gene suppression.

As noted above, in one embodiment, the present invention includes a novel paratransgenic system which may further include a novel method for implementation of an RNAi-based strategy in which natural shrimp symbiotic bacteria are transformed with plasmids that express dsRNA, targeting essential genes that may reduce or eliminate transmission of such pathogens. Such embodiments may have particular application to aquatic organisms in aquaculture environments.

As noted above, aquatic organisms, such as shrimp, possess a natural anti-viral defense mechanism RNA interference (RNAi). Briefly, by use of the exo-siRNA RNAi pathway, shrimp recognize viral long double-stranded (ds) RNA generated during virus replication, digest it to 21-bp short interfering RNA (siRNA) segments with an RNase III family enzyme called Dicer 2, and use these as effectors to identify, cleave and inactivate replicating virus genomes.

Thus, according to one aspect of the present invention, there is provided a method of controlling a pathogenically infected shrimp, the method comprising administering to a shrimp population a genetically modified bacteria expressing a heterologous nucleic acid sequence which specifically downregulates an expression of at least one essential pathogen gene product of the shrimp, wherein downregulation of the expression of the at least one essential pathogen resistance gene may prevent replication and/or pathogenicity of the shrimp pathogen.

In one embodiment, the present invention includes the generation of a novel paratransgenic system for the biocontrol of pathogen-vectors. The invention may specifically include a paratransgenic system configured to deliver one or more inhibitory RNA molecules to pathogen/disease-transmitting organisms. In one embodiment, the invention may include one or more genetically engineered microorganisms configured to deliver one or more inhibitory RNA molecules to aquatic organisms in aquaculture systems. In a preferred embodiment, the invention may include one or more genetically engineered enteric bacteria configured to deliver one or more dsRNA molecules to aquatic organisms in aquaculture systems.

Other embodiments of the current invention include the generation of one or more enteric bacteria that may be endosymbiotic, or act as a probiotic as herein defined, with the target host organism, in this case shrimp. These enteric bacteria may persist in the gut throughout all stages of shrimp development. Another embodiment of the invention includes the generation of one or more enteric bacteria that may be endosymbiotic, or act as a probiotic as herein defined, that are further genetically modified, or transformed, to produce one or more dsRNA (double-stranded) molecules. These dsRNA molecules may correspond to one or more pathogen genes. Moreover, dsRNA molecules may generate an RNA-mediated downregulation or suppression of select viral genes. This RNA-mediated downregulation or suppression of select viral genes may be through an interfering RNA process as generally described here.

Another embodiment includes the generation of one or more enteric bacteria that may be endosymbiotic, or act as a probiotic as herein described, with the target host organism and that may colonize the gut of the target host, and further be configured to continuously deliver dsRNA molecules that correspond to one or more pathogen genes of the white spot syndrome virus (WSSV), or other aquatic pathogens identified herein, and may further elicit an interfering RNA-mediated reaction causing the suppression of the target viral genes.

In one preferred embodiment, the invention may include methods and compositions for the biocontrol of WSSV infection in shrimp. In this preferred embodiment, a shrimp population may be administered a genetically modified bacteria expressing a heterologous nucleic acid sequence which specifically downregulates an expression of at least one essential WSSV gene product, wherein downregulation of the expression of the essential WSSV gene may prevent replication and/or pathogenicity of WSSV in shrimp.

In this preferred embodiment, the heterologous nucleic acid sequence expresses an RNA duplex, comprising a sense region and an antisense region, wherein the antisense region includes a plurality of contiguous nucleotides that are complementary to a messenger RNA sequence encoded by the target gene. In one embodiment, the polynucleotide encoding the siRNA comprises at least one nucleotide sequence configured to generate a hpRNA that targets one or more essential WSSV genes. In this preferred embodiment, such hpRNAs may inhibit expression of target genes in WSSV including, but not limited to: viral capsid protein 19 (vp19), viral capsid protein 19 (vp28), and early non-structural gene (Wsv477) among others. In this embodiment, a heterologous nucleic acid sequence expresses an RNA duplex, or hpRNA, may be selected from the group consisting of: SEQ ID NO.1, SEQ ID NO.2, and SEQ ID NO.3. In this embodiment, SEQ ID NO.1 is configured to target and inhibit expression of an early non-structural gene (Wsv477)(SEQ ID. NO 9 and 10). SEQ ID NO.1 is configured to target and inhibit expression of viral capsid protein 19 (vp28) (SEQ ID. NO 7 and 7), and SEQ ID NO.3 is configured to target and inhibit expression of viral capsid protein 19 (vp19) (SEQ ID. NO 5 and 6). It should be noted that the identification of a DNA sequence also includes the corresponding RNA sequence it encodes. As such, a reference to a SEQ ID NO. that includes DNA also specifically include the sequence of the RNA that it expresses as would be understood by one of ordinary skill in the art. For example, where it is claims that a heterologous inhibitory polynucleotide may be selected from the group consisting of: SEQ ID NO. 1, SEQ ID NO. 2, and/or SEQ ID NO. 3, such a claim may include the sequence of the inhibitory RNA molecule as one of ordinary skill could easily determine without undue experimentation.

In a preferred embodiment, a messenger RNA sequence encoded by the target pathogen gene may include a gene located in a region of higher than average homology, or in other words, a gene fully or partially located in the most conserved region of a pathogens genome, when compared to the sequences of other strains of the pathogens of genes. In one specific embodiment, SEQ ID NO. 1, SEQ ID NO. 2, and SEQ ID NO.3, correspond to highly conserved structural and/or non-structural proteins coding regions in SEQ ID NO. 5-10, generally. Naturally, such sequences are exemplary, as they may be alternatively, redundant or overlapped across one or more distinct gene coding segments.

Figure 2:
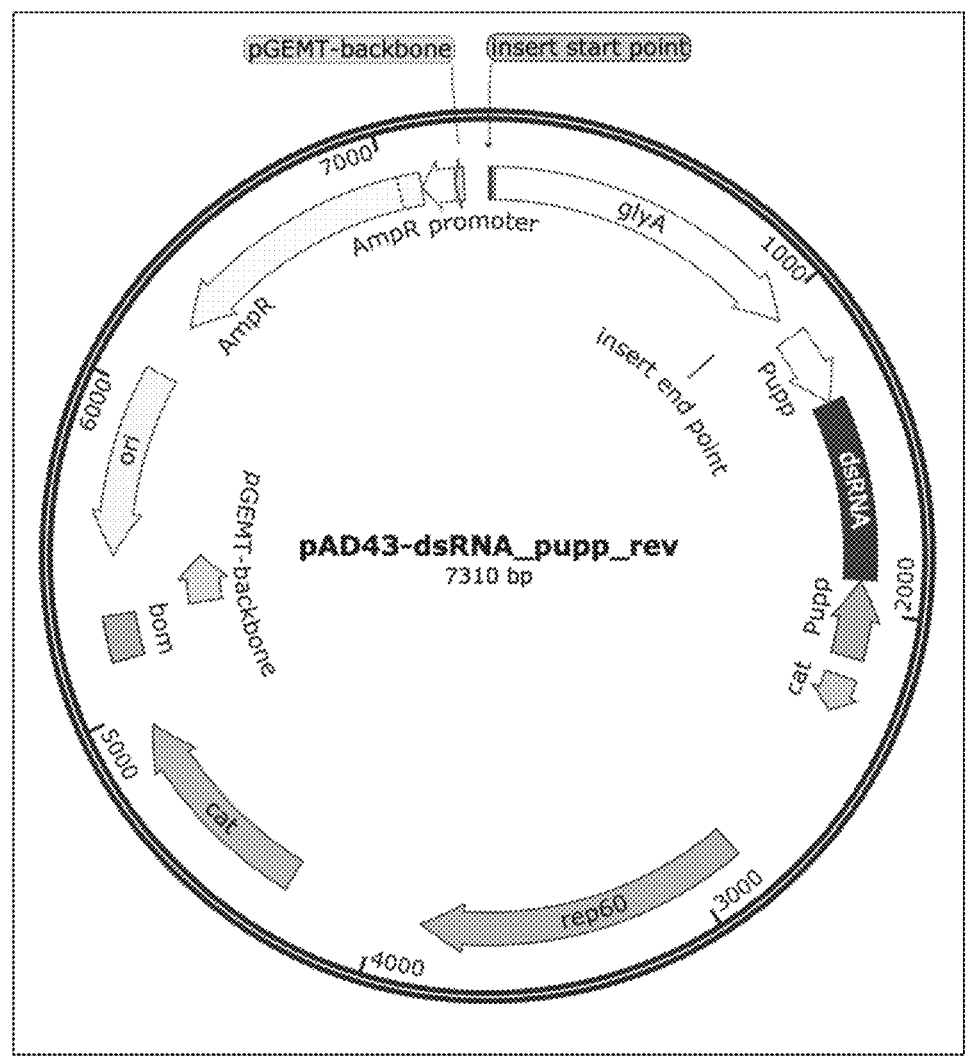
FIG. 2: PAD-dsRNA plasmid map.
Figure 3:
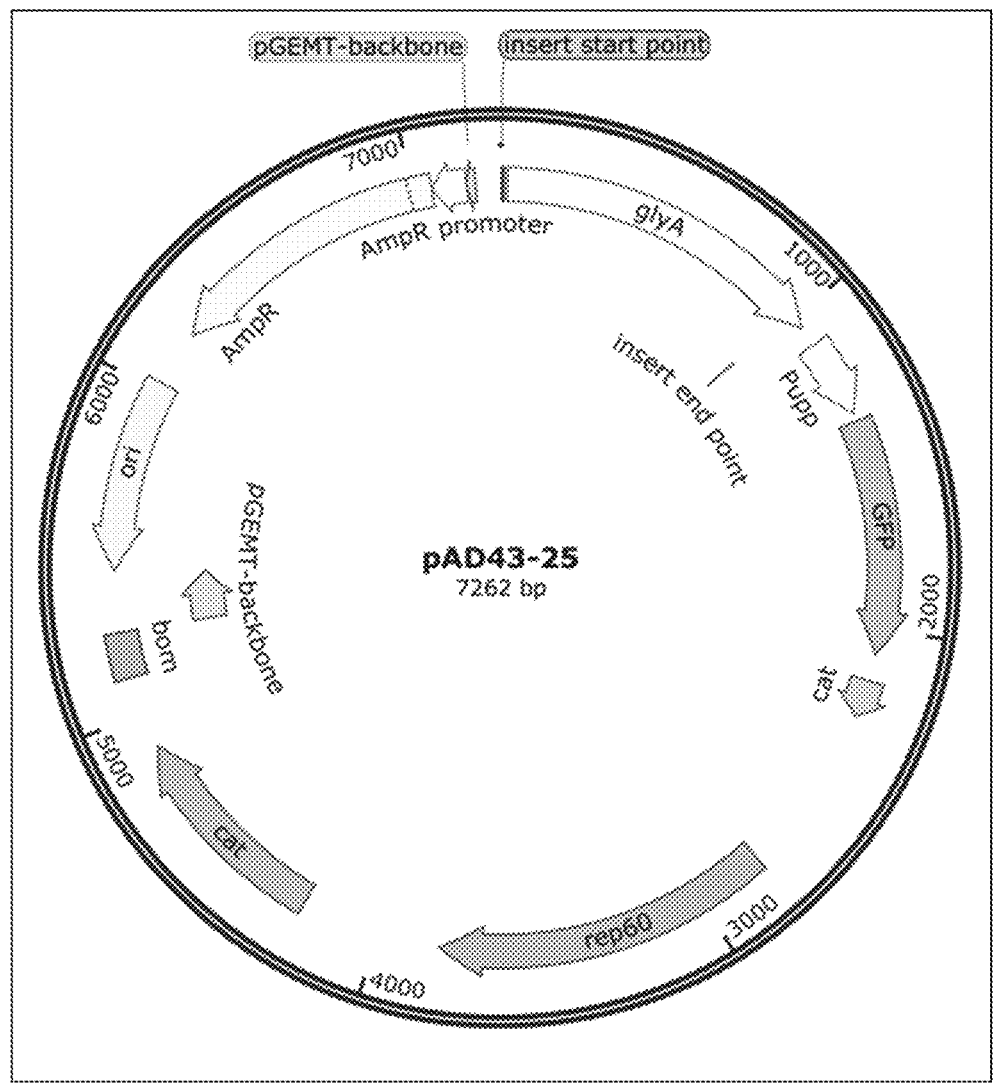
FIG. 3: PAD-43-25 (pGFP expressing) plasmid map.

The present invention may further include one or more vectors for modulating multiple pathogen genes, wherein the vector comprising one, or a plurality of dsRNAs may correspond to one or more select pathogen genes, for example the WSSV genes identified in SEQ ID NO. 6, 8, 10. As generally shown in FIGS. 2-3, this embodiment may include the use of a plasmid expression system. In some embodiments, this plasmid may have one or more expression cassettes, including: at least one gene suppressing cassette containing a polynucleotide operably-linked to a promoter sequence, wherein the polynucleotide encodes an interfering RNA molecule, such as a dsRNA, or a molecule that will subsequently generate interfering RNA molecule, such as a dsRNA, that reduces expression of a target pathogen gene by RNA interference.

A preferred embodiment of the present invention includes a vector for modulating multiple host genes, wherein the vector comprising one, or a plurality of dsRNAs may correspond to one or more select host genes. This embodiment may include the use of a plasmid expression system. In some embodiments, this plasmid may have one or more expression cassettes, including: at least one gene suppressing cassette containing a polynucleotide operably-linked to a promoter sequence, wherein the polynucleotide encodes an interfering RNA molecule, such as a dsRNA, or a molecule that will subsequently generate interfering RNA molecule, such as a dsRNA, that reduces expression of a target host gene by RNA interference.

Another embodiment of the present invention includes a vector for modulating host and pathogen genes, wherein the vector comprising one, or plurality of dsRNAs that may correspond to one or more select host and pathogen genes. This embodiment may include the use of a plasmid expression system. In some embodiments, this plasmid may have one or more expression cassettes, including: at least one gene suppressing cassette containing a first polynucleotide operably-linked to a promoter sequence, wherein the polynucleotide encodes an interfering RNA molecule, such as a dsRNA, or a molecule that will subsequently generate an interfering RNA molecule, such as a dsRNA, that reduces expression of a target host gene by RNA interference. This gene cassette may further contain a second polynucleotide operably-linked to a promoter sequence, wherein the polynucleotide encodes an interfering RNA molecule, such as a dsRNA, or a molecule that will subsequently generate interfering RNA molecule, such as a dsRNA, that reduces expression of a target pathogen gene by RNA interference.

The present invention also includes a vector for inhibiting the expression of viral or bacterial genes in a host, wherein the vector comprises at least one gene suppressing cassette containing a polynucleotide operably-linked to a promoter sequence, wherein the polynucleotide encodes an siRNA molecule that reduces expression of a target pathogen gene within the host by RNA interference. In one embodiment, the polynucleotide encoding the siRNA comprises the nucleotide sequence of SEQ ID NO.2, SEQ ID NO.2, and/or SEQ ID NO.3.

Likewise, the vectors of the present invention can include a plurality of gene suppressing cassettes, wherein each gene suppressing cassette contains a polynucleotide encoding an siRNA molecule, such as a dsRNA, that targets the same mRNA sequence or different mRNA sequences. For example, each gene suppressing cassette can encode a dsRNA molecule that targets an mRNA sequence of two or more different genes. Furthermore, each vector of the present invention can include a plurality of gene promoting cassettes and a plurality of gene suppressing cassettes.

Examples of suitable promoters for gene suppressing cassettes include, but are not limited to, T7 promoter, bla promotor, U6 promoter, pol II promoter, Ell promoter, and CMV promoter and the like. Optionally, each of the promoter sequences of the gene promoting cassettes and the gene suppressing cassettes can be inducible and/or tissue-specific.

An additional aspect of the invention may include novel methods to provide genetically engineered enteric-bacteria that may be configured to colonize an animal gut and prevent viral pathogens from escaping the gut into the surrounding epithelium. More specifically, one aim of the invention may be to introduce genetically engineered enteric-bacteria to a shrimp's gut and be further configured to produce and secrete dsRNA. These dsRNA molecules may be taken up by the surrounding epithelial cells, causing a strong RNAi cascade preventing viral replication, and/or suppressing pathogen levels such that no significant number of virions can migrate from the epithelial cells surrounding the shrimp's gut. In additional embodiments, target epithelial cells may uptake dsRNA secreted by transformed paratransgenic bacteria located in the gut through endocytic, vesicular trafficking, phagocytosis and/or other active or passive polynucleotide transport processes.

The present invention, in some embodiments thereof, relates to isolated nucleic acid agents, and, more particularly, but not exclusively, to the use of the same for controlling pathogenically infected animals, such as shrimp.

According to some embodiments of the invention, an essential gene may include a gene selected from the group consisting of one or more target pathogen genes that are essential to virulence, coat proteins, metabolic activity, infection pathways and/or energy-production and the like. A target gene may include one or more genes that are responsible for pathogenicity, or the capacity to cause a disease condition in the host. Examples of such target genes may also include one or more virulence factors. Examples of such virulence factors may include, but not be limited to:

Adherence Factors: This group may include genes that help bacterial pathogens adhere to certain cells;

Invasion Factors: This group may include genes for surface components that allow the bacterium to invade host cells;

Capsules: This group may include genes for structural capsules that may protect bacteria from opsonization and phagocytosis;

Endotoxins: This group may include genes for several types of toxic lipopolysaccharides that may elicit an immune response;

Exotoxins: This group may include genes for several types of protein toxins and enzymes produced and/or secreted from pathogenic bacteria. Major categories include cytotoxins, neurotoxins, and enterotoxins;

Siderophores: This group may include genes for several types of iron-binding factors that allow some bacteria to compete with the host for iron, which is bound to hemoglobin, transferrin, and lactoferrin;

Host-Conversion Factors: This group may include genes that alter the metabolism of the host to the benefit of the pathogen, including but not limited to evading host defenses.

Structural: This group of genes may include genes encoding viral capsis needed for viral replication.

Non-Structural: This group of genes may include genes encoding non-structural viral proteins needed for viral replication. Example may include genes responsible for viral genome integration and/or replication.

One preferred embodiment of the present invention may include an isolated nucleic acid agent, comprising a polynucleotide expressing a nucleic acid sequence which specifically downregulates an expression of at least one pathogen gene. In a preferred embodiment, this isolated nucleic acid agent may comprise a polynucleotide expressing a dsRNA sequence which specifically downregulates an expression of at least one animal pathogen through a siRNA process. Another embodiment of the present invention may include a nucleic acid construct comprising a nucleic acid sequence encoding the isolated nucleic acid agent, such as a dsRNA or a nucleic acid agent that may form into a dsRNA, in some embodiments of the invention.

According to alternative embodiments of the invention, the nucleic acid sequence directly corresponds with a pathogen gene, while in alternative embodiments the nucleic acid sequence corresponds, or overlaps with one or more pathogen genes. According to some embodiments of the invention, the dsRNA nucleic acid sequence directly corresponds with a pathogen gene, while in alternative embodiments the dsRNA nucleic acid sequence corresponds, or overlaps with one or more pathogen genes.

As noted above, the inventive technology may be applied to a variety of organisms, both plant and animal. For example, the invention may comprise dsRNA-mediated disease control systems that may be configured to inactivate one or more pathogen gene targets in any appropriate host organism. In one specific embodiment, one or more inhibitory RNA molecules, in this instance dsRNA, may be delivered to a target host/population of vertebrate and invertebrate animals. For example, poultry such as: chicken, turkey, duck and geese (see Table 4), bees (see FIG. 5) as well as mammals (see FIG. 6), including humans, through genetically modified enteric bacteria that may naturally, or be configured to colonize in the gut of the host.

In this exemplary embodiment, the colonized bacteria may express inhibitory RNA molecules, such as dsRNA/shRNAs, that may further be processed by the host's DICER/RISC complex allowing pathogen-specific mRNA silencing/inactivation of essential pathogen genes. Examples of some poultry specific pathogens that may be targeted by the invention are listed in tables 4-6 below. These colonized enteric bacteria, having become a part of the host's natural microbiome, may continuously deliver the dsRNA molecules via the intestine during various stages of the development providing pathogen-specific mRNA silencing/inactivation of essential pathogen genes throughout the host's lifecycle. In addition, as the enteric bacteria vector may be an already naturally occurring part of the poultry's or bee's microbiome, its presence will not pose any risk to the organism, environment or end-consumers, nor will allow for vertical transmission to progeny and horizontal transmission to host population at large through the distribution of the modified bacteria excreted into the environment as waste.

In certain embodiments, a probiotic bacteria may be configured to express one or more interfering RNA molecules. In this preferred embodiment, a subject, such as a human, may take a therapeutic or effective amount of the probiotic which may act as a vaccine or antibiotic or anti-viral pharmaceutical. Production, and delivery of such probiotic bacteria is well known and would be within the skill on those generally skilled in the art.

The term "aquaculture" as used herein includes the cultivation of aquatic organisms under controlled conditions.

The term "aquatic organism" and/or "aquatic animal" as used herein include organisms grown in water, either fresh or saltwater. Aquatic organisms/animals includes vertebrates, invertebrates, arthropods, fish, mollusks, including, shrimp (e.g., penaeid shrimp, *Penaeus esculentu, Penaeus setiferus, Penaeus stylirostris, Penaeus occidentalis, Penaeus japonicus, Penaeus vannamei, Penaeus monodon, Penaeus chinensis, Penaeus aztecus, Penaeus* duorarum, *Penaeus indicus*, and *Penaeus merguiensis, Penaeus californiensis, Penaeus semisulcatus, Penaeus monodon*, brine shrimp, freshwater shrimp, etc), crabs, oysters, scallop, prawn clams, cartilaginous fish (e.g., sea bream, trout, bass, striped bass, tilapia, catfish, salmonids, carp, catfish, yellowtail, carp zebrafish, red drum, etc), crustaceans, among others. Shrimp include, shrimp raised in aquaculture as well.

The term "probiotic" refers to a microorganism, such as bacteria, that may colonize a host for a sufficient length of time to delver a therapeutic or effective amount of an interfering RNA molecule. A probiotic may include endosymbiotic bacteria, or naturally occurring flora that may permanently to temporarily colonize an animal, such as an aquatic organism. Probiotic organisms may also include algae, and fungi, such as yeast.

Specific examples of bacterial vectors include bacteria (e.g., cocci and rods), filamentous algae and detritus. Specific embodiments of transformable bacterial vectors cells that may be endogenous through all life cycles of the host may include all those listed herein. Additional embodiments may include one or more bacterial strains selected from the examples listed herein. Naturally, such a list is not exclusive, and is merely exemplary of certain preferred embodiments of paratransgenic bacterial strains.

As used herein, the phrase "host" refers to an animal carrying a disease-causing pathogen, an animal susceptible to a disease-causing pathogen, an animal population where members are carrying a disease-causing pathogen, or an animal population where members are susceptible to a disease-causing pathogen. These include hosts listed in tables 4-6, and elsewhere.

As used herein, "pathogen" refers to a disease causing agent. These include the pathogens included in tables 4-6, and elsewhere.

As used herein, "vaccine" refers to compositions that result in both active and passive immunizations. Both polynucleotides and their expressed gene products are referred to as vaccines herein. A feed including a treated bacteria configured to express an interfering bacteria may also be a vaccine. Feeding treated feed to an animal may be a vaccination.

As used herein, the phrase "feed" refers to animal consumable material introduced as part of the feeding regimen or applied directly to the water in the case of aquatic animals. A "treated feed" refers to a feed treated with a treated bacteria configured to express an interfering bacteria.

As used herein, the term "controlling" and/or "bio-control" refers to reducing and/or regulating pathogen/disease progression and/or transmission.

The term "nucleic acid" as used herein, refers to a polymer of ribonucleotides or deoxyribonucleotides. Typically, "nucleic acid or "nucleic acid agent" polymers occur in either single or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed, over-expressed, under expressed or not expressed at all.

The terms "genetically modified," "bio-transformed," "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e., organism not subjected to the mutagens). Also, an organism that has been bred to incorporate a mutation into its genetic material is a genetically altered organism.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An "expression vector" is a nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, expression vectors are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassette assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is "operably linked to an expression control sequence(s)" (e.g., a promoter and, optionally, an enhancer) when the expression control sequence controls and regulates the transcription and/or translation of that polynucleotide sequence. As used herein, the phrase "gene product" refers to an RNA molecule or a protein.

This invention utilizes routine techniques in the field of molecular biology. Basic texts disclosing the general methods of use in this invention include Green and Sambrook, 4th ed. 2012, Cold Spring Harbor Laboratory; Kriegler, Gene Transfer and Expression: A Laboratory Manual (1993); and Ausubel et al., eds., Current Protocols in Molecular Biology, 1994-current, John Wiley & Sons. Unless otherwise noted, technical terms are used according to conventional usage. Definitions of common terms in molecular biology maybe found in e.g., Benjamin Lewin, Genes IX, published by Oxford University Press, 2007 (ISBN 0763740632); Krebs, et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The present teachings contemplate the targeting of homologs and orthologs according to the selected host species. Homologous sequences include both orthologous and paralogous sequences. The term "paralogous" relates to gene-duplications within the genome of a species leading to paralogous genes. The term "orthologous" relates to homologous genes in different organisms due to ancestral relationship. Thus, orthologs are evolutionary counterparts derived from a single ancestral gene in the last common ancestor of given two species (Koonin EV and Galperin MY (Sequence—Evolution—Function: Computational Approaches in Comparative Genomics. Boston: Kluwer Academic; 2003. Chapter 2, Evolutionary Concept in Genetics and Genomics. Available from: ncbi(dot)nlm(dot)nih (dot)gov/books/NBK20255) and therefore have great likelihood of having the same function. As such, orthologs usually play a similar role to that in the original species in another species.

Homology (e.g., percent homology, sequence identity+ sequence similarity) can be determined using any homology comparison software computing a pairwise sequence alignment. As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9], According to a specific embodiment, the homolog sequences are at least 60%, 65%, 70%, 75%, 80%, 85%, 90%, 95% or even identical to the sequences (nucleic acid or amino acid sequences) provided herein. Homolog sequences of SEQ ID Nos 1-6 of between 50%-99% may be included in certain embodiments of the present invention.

Downregulating expression of a pathogen resistance gene product of a host can be monitored, for example, by direct detection of gene transcripts (for example, by PCR), by detection of polypeptide(s) encoded by the gene (for example, by Western blot or immunoprecipitation), by detection of biological activity of polypeptides encode by the gene (for example, catalytic activity, ligand binding, and the like), or by monitoring changes in the hosts (for example, reduced mortality of the host etc). Additionally or alternatively downregulating expression of a pathogen resistance gene product may be monitored by measuring pathogen levels (e.g. viral levels, bacterial levels etc.) in the host as compared to wild type (i.e. control) hosts not treated by the agents of the invention.

As generally noted above, according to some aspects of the invention, there is provided an isolated nucleic acid agent comprising a nucleic acid sequence, which specifically downregulates the expression of at least one host pathogen resistance gene product. According to one embodiment, the agent is a polynucleotide agent, such as an RNA silencing agent. In a preferred embodiment, the agent is a polynucleotide agent, such as dsRNA, configured to induce RNA interference.

As used herein, the term "interfering RNA molecules" or "interfering RNA" refers to an RNA which is capable of inhibiting or "silencing" the expression of a target gene. In certain embodiments, the RNA silencing agent is capable of preventing complete processing (e.g. the full translation and/or expression) of an mRNA molecule through a post-transcriptional silencing mechanism. RNA silencing agents include noncoding RNA molecules, for example RNA duplexes comprising paired strands, as well as precursor RNAs from which such small noncoding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

In some embodiments of the invention, the nucleic acid agent is a double stranded RNA (dsRNA). As used herein the term "dsRNA" relates to two strands of anti-parallel polyribonucleic acids held together by base pairing. Examples include SEQ ID NOs 1-5. The two strands can be of identical length or of different lengths provided there is enough sequence homology between the two strands that a double stranded structure is formed with at least 60%, 70% 80%, 90%, 95% or 100% complementary over the entire length. According to an embodiment of the invention, there are no overhangs for the dsRNA molecule. According to another embodiment of the invention, the dsRNA molecule comprises overhangs. According to other embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed.

It will be noted that the dsRNA can be defined in terms of the nucleic acid sequence of the DNA encoding the target gene transcript, and it is understood that a dsRNA sequence corresponding to the coding sequence of a gene comprises an RNA complement of the gene's coding sequence, or other sequence of the gene which is transcribed into RNA.

The inhibitory RNA sequence can be greater than 90% identical, or even 100% identical, to the portion of the target gene transcript. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60 degrees C. hybridization for 12-1b hours; followed by washing). The length of the double-stranded nucleotide sequences complementary to the target gene transcript may be at least about 18, 19, 21, 25, 50, 100, 200, 300, 400, 491, 500, 550, 600, 650, 700, 750, 800, 900, 1000 or more bases. In some embodiments of the invention, the length of the double-stranded nucleotide sequence is approximately from about 18 to about 530, or longer, nucleotides in length.

The present teachings relate to various lengths of dsRNA, whereby the shorter version i.e., x is shorter or equals 50 bp (e.g., 17-50), is referred to as siRNA or miRNA. Longer dsRNA molecules of 51-600 are referred to herein as dsRNA, which can be further processed for siRNA molecules. According to some embodiments, the nucleic acid sequence of the dsRNA is greater than 15 base pairs in length. According to yet other embodiments, the nucleic acid sequence of the dsRNA is 19-25 base pairs in length, 30-100 base pairs in length, 100-250 base pairs in length or 100-500 base pairs in length. According to still other embodiments, the dsRNA is 500-800 base pairs in length, 700-800 base pairs in length, 300-600 base pairs in length, 350-500 base pairs in length or 400-450 base pairs in length. In some embodiments, the dsRNA is 400 base pairs in length. In some embodiments, the dsRNA is 750 base pairs in length.

The term "siRNA" refers to small inhibitory RNA duplexes (generally between 17-30 base pairs, but also longer e.g., 31-50 bp) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC. It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

In certain embodiment, dsRNA can come from 2 sources; one derived from gene transcripts generated from opposing gene promoters on opposite strands of the DNA and 2) from fold back hairpin structures produced from a single gene promoter but having internal complimentary. For example, strands of a double-stranded interfering RNA (e.g., a siRNA) may be connected to form a hairpin or stem-loop structure (e.g., a shRNA). Thus, as mentioned the RNA silencing agent may also be a short hairpin RNA (shRNA). The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550, SEQ ID NO. 302) and 5'-UUU-GUGUAG-3' (Castanotto, D. et al. (2002) RNA 8:1454, SEQ ID NO. 303). It will be recognized by one of skill in the art that the resulting single chain oligonucleotide forms a stem-loop or hairpin structure comprising a double-stranded region capable of interacting with the RNAi machinery.

As used herein, the phrase "microRNA" (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence, essentially complementary to the nucleotide sequence of the miRNA molecule. Typically, a miRNA molecule is processed from a "pre-miRNA" or as used herein a precursor of a pre-miRNA molecule by proteins, such as DCL proteins, and loaded onto a RISC complex where it can guide the cleavage of the target RNA molecules. Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides, which can adopt a secondary structure comprising an imperfect double stranded RNA stem and a single stranded RNA loop (also referred to as "hairpin"), and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nucleotides in length. The complementarity between the miRNA and its complement need not be perfect, and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand, which at its 5' end, is the least involved in hydrogen bonding between the nucleotides of the different strands of the cleaved dsRNA stem, is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bonds, or G and U involving two hydrogen bonds is less strong that between G and C involving three hydrogen bonds.

Naturally occurring miRNA molecules may be comprised within their naturally occurring pre-miRNA molecules, but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA.

According to the present teachings, the dsRNA molecules may be naturally occurring or synthetic. The dsRNA can be a mixture of long and short dsRNA molecules such as, dsRNA, siRNA, siRNA+dsRNA, siRNA+miRNA, or a combination of same.

In a preferred embodiment, one or more nucleic acid agents are designed for specifically targeting a target gene of interest (e.g. a pathogen non-structural gene). It will be appreciated that the nucleic acid agent can be used to downregulate one or more target genes (e.g. as described in detail above). If a number of target genes are targeted, a heterogenic composition which comprises a plurality of nucleic acid agents for targeting a number of target genes is used. Alternatively the plurality of nucleic acid agents is separately formulated. According to a specific embodiment, a number of distinct nucleic acid agent molecules for a single target are used, which may be used separately or simultaneously (i.e., co-formulation) applied.

For example, in order to silence the expression of an mRNA of interest, synthesis of the dsRNA suitable for use with some embodiments of the invention can be selected as follows. First, the mRNA sequence is scanned including the 3' UTR and the 5' UTR. Second, the mRNA sequence is compared to an appropriate genomic database using any sequence alignment software, such as the BLAST software available from the NCBI. Putative regions in the mRNA sequence which exhibit significant homology to other coding sequences are filtered out. Qualifying target sequences are selected as templates for dsRNA synthesis. Preferred sequences are those that have as little homology to other genes in the genome as to reduce an "off-target" effect.

It will be appreciated that the RNA silencing agent of some embodiments of the invention need not be limited to those molecules containing only RNA, but further encompasses chemically-modified nucleotides and non-nucleotides.

According to one embodiment, the dsRNA specifically targets a gene selected from the group consisting of SEQ ID Nos 1-4 or a variant of homolog thereof. In addition, the term AMPLICON means a piece of DNA or RNA.

In certain embodiments, expression of the dsRNA molecule doesn't require a cis-acting regulatory sequence (e.g., heterologous) transcribing the dsRNA. As used herein, the term "heterologous" refers to exogenous, not-naturally occurring within a native cell of the host or in a cell in which the dsRNA is fed to a host (such as by position of integration, or being non-naturally found within the cell).

The nucleic acid agent can be further comprised within a nucleic acid construct comprising additional regulatory elements. For example, transcription from an expression cassette, a regulatory region (e.g., promoter, enhancer, silencer, leader, intron and polyadenylation) may be used to modulate the transcription of the RNA strand (or strands). Therefore, in one embodiment, there is provided a nucleic acid construct comprising the nucleic acid agent. The nucleic acid construct can have polynucleotide sequences constructed to facilitate transcription of the RNA molecules of the present invention operably linked to one or more promoter sequences functional in a host cell. The polynucleotide sequences may be placed under the control of an endogenous promoter normally present in the host genome. The polynucleotide sequences of the present invention, under the control of an operably linked promoter sequence, may further be flanked by additional sequences that advantageously effect its transcription and/or the stability of a resulting transcript. Such sequences are generally located upstream of the promoter and/or downstream of the 3' end of the expression construct. The term "operably linked," as used in reference to a regulatory sequence and a structural nucleotide sequence, means that the regulatory sequence causes regulated expression of the linked structural nucleotide sequence.

Genetic "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

It will be appreciated that the nucleic acid agents can be delivered to the animal, such as a shrimp in a variety of ways. According to one embodiment, the composition of some embodiments comprises cells, which comprise the nucleic acid agent. As used herein, the term "cell" or "cells," with respect to a host may refer to an animal cell in any stage of its lifecycle. In a certain embodiment, the paratransgenic system may establish genetically modified bacteria that may be endogenous through all life cycles of the host. According to a specific embodiment, the cell is a bacterial cell.

In a further embodiment, a composition including a genetically modified bacteria configured to express dsRNA may be formulated as feed and/or a water dispersible granule or powder that may further be configured to be dispersed into the environment. In yet a further embodiment, the compositions of the present invention may also comprise a wettable powder, spray, emulsion, colloid, aqueous or organic solution, dust, pellet, or colloidal concentrate. Dry forms of the compositions may be formulated to dissolve immediately upon wetting, or alternatively, dissolve in a controlled-release, sustained-release, or other time-dependent manner.

Alternatively or additionally, the composition may comprise an aqueous solution. Such aqueous solutions or suspensions may be provided as a concentrated stock solution which is diluted prior to application, or alternatively, as a diluted solution ready-to-apply. Such compositions may be formulated in a variety of ways. They may be employed as wettable powders, granules or dusts, by mixing with various inert materials, such as inorganic minerals (silicone or silicon derivatives, phyllosilicates, carbonates, sulfates, phosphates, and the like) or botanical materials (powdered corncobs, rice hulls, walnut shells, and the like). The formulations or compositions containing paratransgenic bacteria may include spreader-sticker adjuvants, stabilizing agents, other pesticidal additives, or surfactants. Liquid formulations may be employed as foams, suspensions, emulsifiable concentrates, or the like. The ingredients may include Theological agents, surfactants, emulsifiers, dispersants, or polymers.

According to one embodiment, the composition is administered to the host by feeding. Feeding the host with the composition can be effected once, regularly, or semi-regularly over the span of hours, days, weeks, months or even years.

As mentioned, the dsRNA of the invention may be administered as a naked dsRNA. Alternatively, the dsRNA of the invention may be conjugated to a carrier known to one of skill in the art, such as a transfection agent e.g. PEI or chitosan or a protein/lipid carrier or coupled to nanoparticles. The compositions may be formulated prior to administration in an appropriate means such as lyophilized, freeze-dried, microencapsulated, desiccated, or in an aqueous carrier, medium or suitable diluent, such as saline or other buffer. Suitable agricultural carriers can be solid, semi-solid or liquid and are well known in the art. Such compositions may be considered "agriculturally-acceptable carriers", which may covers all adjuvants, e.g., inert components, dispersants, surfactants, tackifiers, binders, etc. that are ordinarily used in pesticide formulation technology.

According to some embodiments, the nucleic acid agent is provided in amounts effective to reduce or suppress expression of at least one host pathogen resistance gene product. As used herein "a suppressive amount" or "an effective amount" or a "therapeutically effective amount" refers to an amount of dsRNA which is sufficient to down-regulate (reduce expression of) the target gene by at least 20%, 30%, 40%, 50%, or more, say 60%, 70%, 80%, 90% or more even 100%, or reduce mortality in an animal or animal population, such as shrimp in aquaculture by at least a measurable percentage, preferably between 1%-100%.

Testing the efficacy of gene silencing can be affected using any method known in the art. For example, using quantitative RT-PCR measuring gene knockdown. Thus, for example, host animals from each treatment group can be collected and pooled together. RNA can be extracted therefrom and cDNA syntheses can be performed. The cDNA can then be used to assess the extent of RNAi, by measuring levels of gene expression using qRT-PCR. Reagents of the present invention can be packed in a kit including the nucleic acid agent (e.g. dsRNA), instructions for administration of the nucleic acid agent, construct or composition to a specific host.

As used herein, the term "gene" or "polynucleotide" refers to a single nucleotide or a polymer of nucleic acid residues of any length. The polynucleotide may contain deoxyribonucleotides, ribonucleotides, and/or their analogs, and may be double-stranded or single stranded. A polynucleotide can comprise modified nucleic acids (e.g., methylated), nucleic acid analogs or non-naturally occurring nucleic acids and can be interrupted by non-nucleic acid residues. For example, a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition, are nucleic acid polymers that have been modified, whether naturally or by intervention.

Constructs of the invention may be prepared by any method known in the art for the synthesis of DNA and RNA molecules, including techniques for chemically synthesizing oligodeoxyribonucleotides and oligoribonucleotides well known in the art, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

As used herein, the terms "approximately" or "about" refer to ±10%. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references, unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Generation of Expression Vectors and Genetically Modified Bacterial Strain Plasmids for dsRNA expression were made by cloning dsRNA sequence between 2 converging pUpp promoters in pAD-43-25 plasmid. As generally shown in FIGS. 2-3, PAD-dsRNA plasmid map and PAD-43-25 (pGFP expressing) plasmid map were generated by the present inventors. RNase III deficient *Bacillus subtilis* strain BG322 was transformed with pAD-dsRNA plasmids (3 plasmids for WSSV-specific dsRNA expression—pAD-dsWsv477 (SEQ ID NO. 1), pAD-dsVp28 (SEQ ID NO. 2), pAD-dsVp19 (SEQ ID NO. 3), and plasmid for expression of unspecific dsLuc pAD-dsLuc (SEQ ID NO. 4).

Example 2: Preparation of Shrimp Feed Containing Genetically Modified Bacteria Bacteria were grown overnight in LB with 5 mg/ml chloramphenicol, and then centrifuged and mixed into a common commercial shrimp feed (Zeigler PL 40) at a concentration of 1E+08 CFU/gm feed and refrigerated. Prepared feed was fed to one gram shrimp at 10% body weight, divided into three feedings per day.

Example 3: Colonization and Persistence of Genetically Modified Bacteria in Shrimp Intestine The present inventors have demonstrated that the exemplary genetically modified *B. subtilis* strain BG322 is able to colonize and persist in shrimp intestines. In this embodiment, the present inventors transformed BG322 with plasmid pAD-43-25 encoding the fluorescent GFP protein. Shrimp were provided feed containing BG322 pAD-43-25 for 10 days and presence of BG322 was detected at days 5 and 10 by analysis of shrimp intestines under fluorescent microscope (GFP fluorescence detected in the intestines) and by plate count method (BG322 colonies were identified by GFP fluorescence) using isolated guts of shrimp. After 5 days of BG322 feeding the bacterial titer in the BG322 intestines was ~1.1E+06 cfu/g and it stayed at approximately the same tier on day 10 (Table 1). Since the bacteria concentration in shrimp intestines became constant after 5 days of feeding, day 5 after feeding bacteria was chosen by the present inventors as an appropriate day for beginning the viral challenges.

Example 4: Introduction of dsRNA Expression Vectors to Shrimp

SPF shrimp (Shrimp Improvement System, Islamorada, Fla.) 1 g weight were maintained in 7 gallon aquariums (n=12). Shrimp were randomly assigned to five treatments groups: 1) shrimp fed with commercial food, no virus injections; 2) shrimp fed with commercial food with BG322 pAD-dsLuc/virus injections; 2) shrimp fed commercial feed with BG322 pAD-dsVp19/virus injections; 3) shrimp fed by commercial food with BG322 pAD-dsVp28/virus injections; 4) shrimp fed by commercial food with BG322 pAD-dsWsv477/virus injections and 5) shrimp fed with commercial food with BG322 pAD-dsLuc/virus injections. Bacteria were provided to shrimp for 5 days before viral injection and during the course of the challenge via feed. Such shrimp being generally referred to as "treated shrimp."

Example 5: WSSV Challenge in dsRNA Expressing (Treated) Shrimp

The present inventors exposed treated shrimp to WSSV by injection of inoculant derived from infected tissues (Ecuador 2001 strain) of shrimp and stored at −80° C. The tissues were homogenized in a blender in a 1:10 ratio of tissue to UV treated chilled salt well water for 30 sec. The preparation was poured into a 50 ml tube and centrifuged for 10 minute at 2500 RPM at 4° C. The resulting supernatant was filtered with a 0.45 μm (PES) filter (Whatman Puradisc®). The filtrate was injected intramuscularly between the second and third tail segment at 20 μl/g body weight of shrimp immediately after preparation.

Example 6: WSSV-Induced Mortality Count in dsRNA Expressing (Treated) Shrimp Mortality count was performed by the present inventors at day 7-10 after the viral injection. In this embodiment, 6 biological replicates (separate tanks) were analyzed for negative control group (no virus), 4 replicates for shrimp fed by dsLuc (non-specific dsRNA), and 5 replicates for each shrimp group fed by BG322-dsVp19, BG322-dsVp28 or BG322-dsWsv477 (anti-WSSV specific dsRNA).

Figure 1:
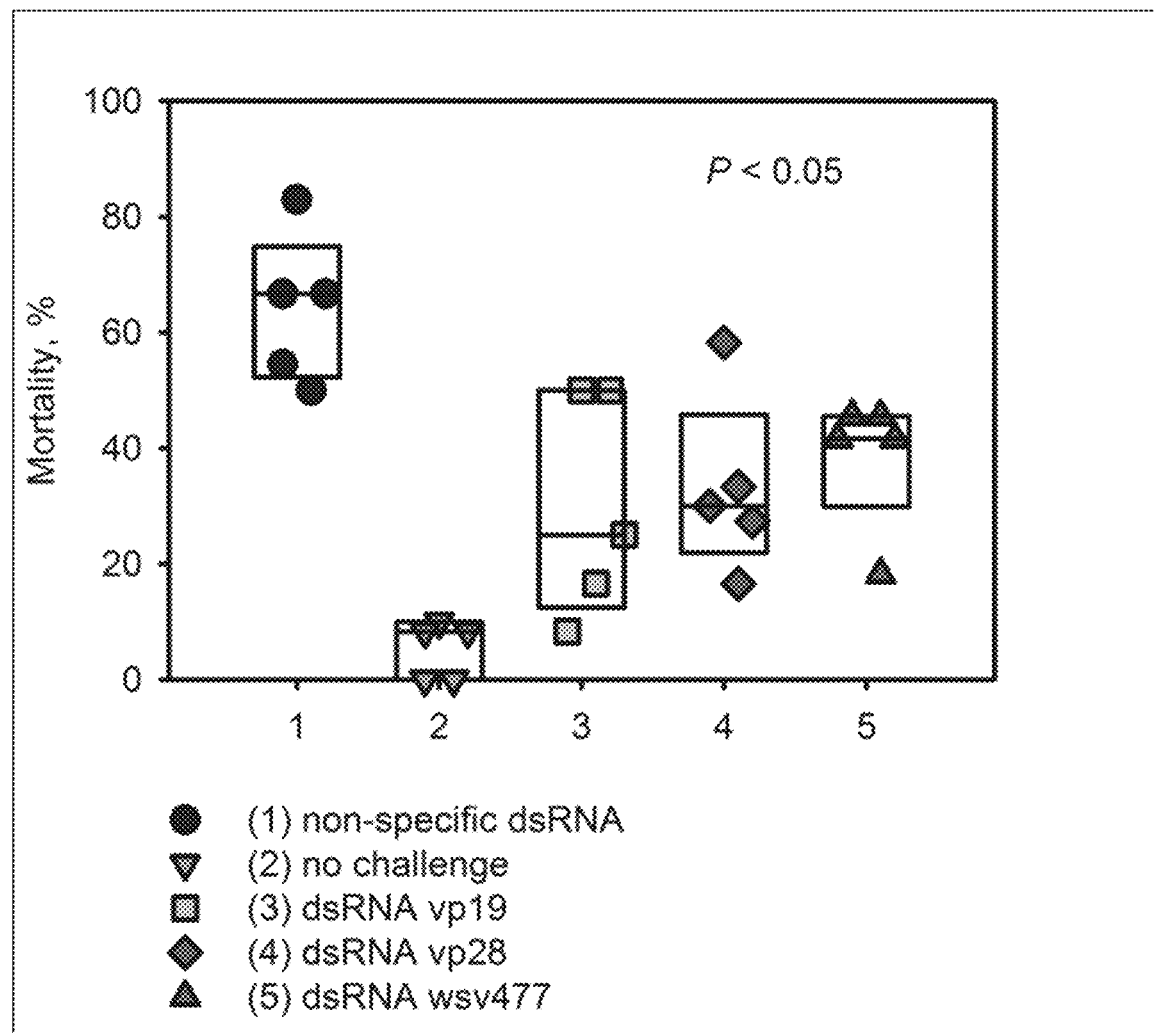
FIG. 1: Total mortality on last day of viral challenge for shrimp fed by BG322 expressing unspecific dsLuc dsRNA or dsRNA specific to WSSV: i) dsVp19 (SEQ ID NO. 3); ii) dsVp28 (SEQ ID NO. 2); and iii) dsWsv477 (SEQ ID NO. 1)

Mortality count from last days of time-course shows ~50% reduction in mortality in shrimp fed by WSSV-targeting dsRNA compared to shrimp fed by unspecific dsRNA. The present inventors further demonstrated 30%, 33% or 38% average mortality was observed in shrimp fed by dsVp19, dsVp28 and dsWsv477 correspondently, while dsLuc fed group had 64% mortality. This difference is statistically significant for p<0.05 (FIG. 1). As such, the present inventors demonstrate that BG322 expressing virus-specific dsRNA provide shrimp protection from the virus.

Example 7: Sequence-Specific Inhibition of WSSV Replication in Shrimp Fed by BG322 Expressing WSSV-Targeting DNA The present inventors used qPCR to evaluate the level of virus replication in shrimp after 10 days of WSSV challenge. Survivors from groups fed BG322-dsLuc, BG322-dsVp19, BG322-dsVp28 and BG322-dsWsv477 were used for total DNA extraction (n=4-6). Total DNA was extracted with Invitrogen Tissue DNA kit, and the concentration of the extracted DNAs was quantified using a NanoDrop ND-100 spectrophotometer (NanoDrop Technologies). 50-100 ng of total DNA was used as a template for qPCR. SybrGreen assay was carried out with SybrGreen PowerUp master Mix. Primers WSSV1011(5') and WSSV1079 (3') generating 69 bp replicon were used for the reaction (Table 2) (Durand et all, 2002). Cycling conditions were as follows: 1 initial step at 95° C. for 10 min followed by 40 cycles of 95° C. for 30 s, 58° C. for 30 s and 72° C. for 30 s. Melting temperature of each sample was examined to verify the purity of the PCR products. PCR reactions were performed on Stratagene Mx3005 real-time PCR system and analyzed with Mx3005 software. For comparison, resulting numbers were normalized to readings from shrimp fed by BG322-dsLUC (positive control group).

Figure 4:
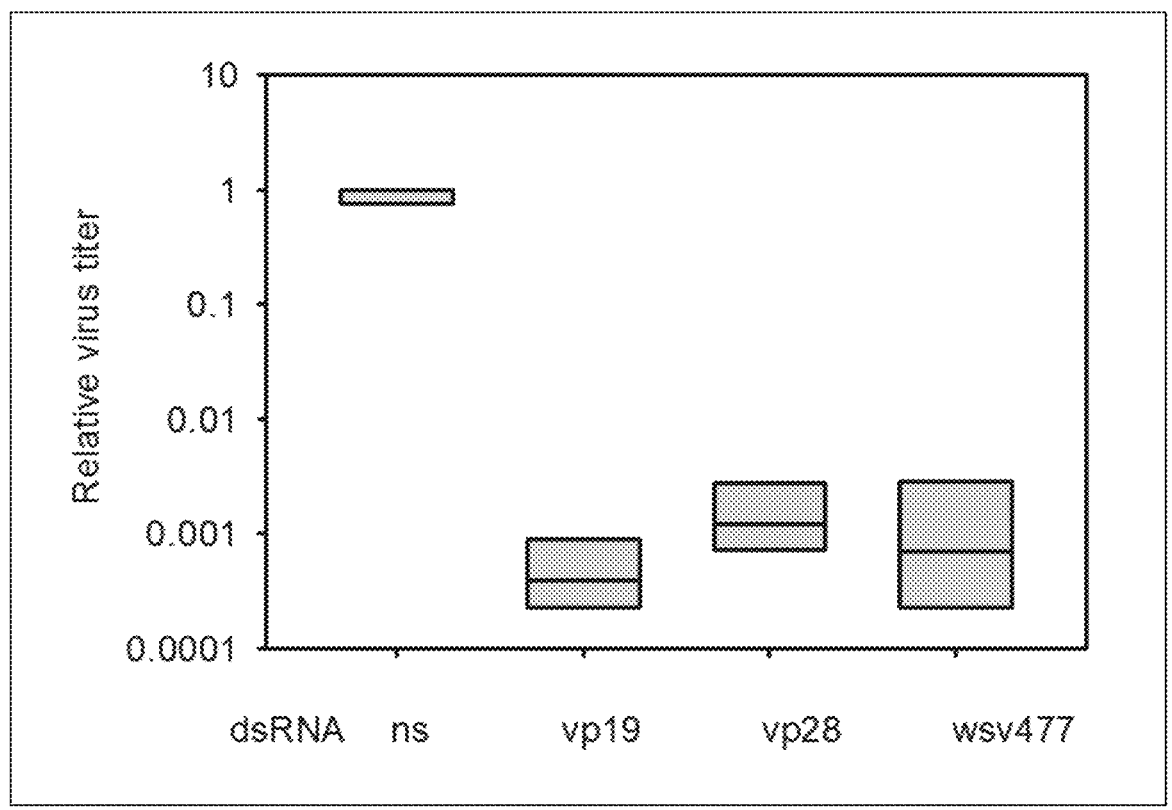
FIG. 4: Relative WSSV titer in shrimp fed by BG322 expressing unspecific dsLuc dsRNA or dsRNA specific to WSSV (dsVp19, dsVp28 and dsWsv477) at day 10 after WSSV injection. Viral copy numbers were adjusted to log 10 scale to allow graphical representation of all groups on the same scale.

The present inventors observed a log 3-4 fold reduction in the amount of virus detected in all shrimp groups fed bacteria expressing WSSV-gene (VP19, VP28, wsv477) targeting dsRNA compared to the amount of virus in shrimp fed bacteria expressing unspecific dsLuc dsRNA (negative control). The difference between unspecific dsRNA group and other groups is statistically significant at p<0.01 as demonstrated generally in FIG. 4.

Example 8: Detection of Antiviral vp19 siRNA in WSSV-Infected Shrimp

The present inventors demonstrated the accumulation of bacteria-specific smallRNA through Northern blotting analysis of smallRNA samples purified from BGG322 vp19-fed shrimps that survived infection by WSSV.

In this embodiment, the present inventors prepared DIG 3' end-labeled probes directed to small RNAs. Sequences of DNA oligonucleotides complimentary to the vp19 dsRNA are presented in Table 3. The probes were ordered via IDTDNA and labeled with the DIG oligonucleotide 3'-end labeling kit. Reaction was stopped by addition of 200 mM EDTA (pH 8.0). Labeled DNA probes were stored at −20° C.

Total RNAs were isolated from the shrimp muscle samples by use of E.Z.N.A miRNA isolation kit (Omega) according to the manufacturer's instructions. The quality and integrity of total RNAs were evaluated by electrophoresis on 15% polyacrylamide-8 M urea gels. The concentration of the extracted RNAs was quantified using a NanoDrop ND-100 spectrophotometer (NanoDrop Technologies). At least 10 μg of total RNA were electrophoresed in a denaturing 15% polyacrylamide gel containing 8 M urea and transferred to a positively charged nylon membrane (Roche). After cross-linking with UV, the membrane was prehybridized in PerfectHyb (Sigma) for 1 h and then hybridized with a digoxigenin (DIG)-labeled DNA probes complementary to dsRNA sequence for 20 h at 44° C. The membranes were washed four subsequent times with SSC wash buffers supplemented with 0.1% SDS (2×, 0.5×, and 0.1×, respectively). Signal detection was performed following the instructions for a DIG High Prime DNA labeling and detection starter kit II (Roche). ssRNA markers of 14 nt, 18 nt, 22 nt, 26 nt and 30 nt were used as markers of small RNA (Takara). Finally, the hybridization signals were visualized by BIO-RAD ChemiDoc XRS.

Figure 5:
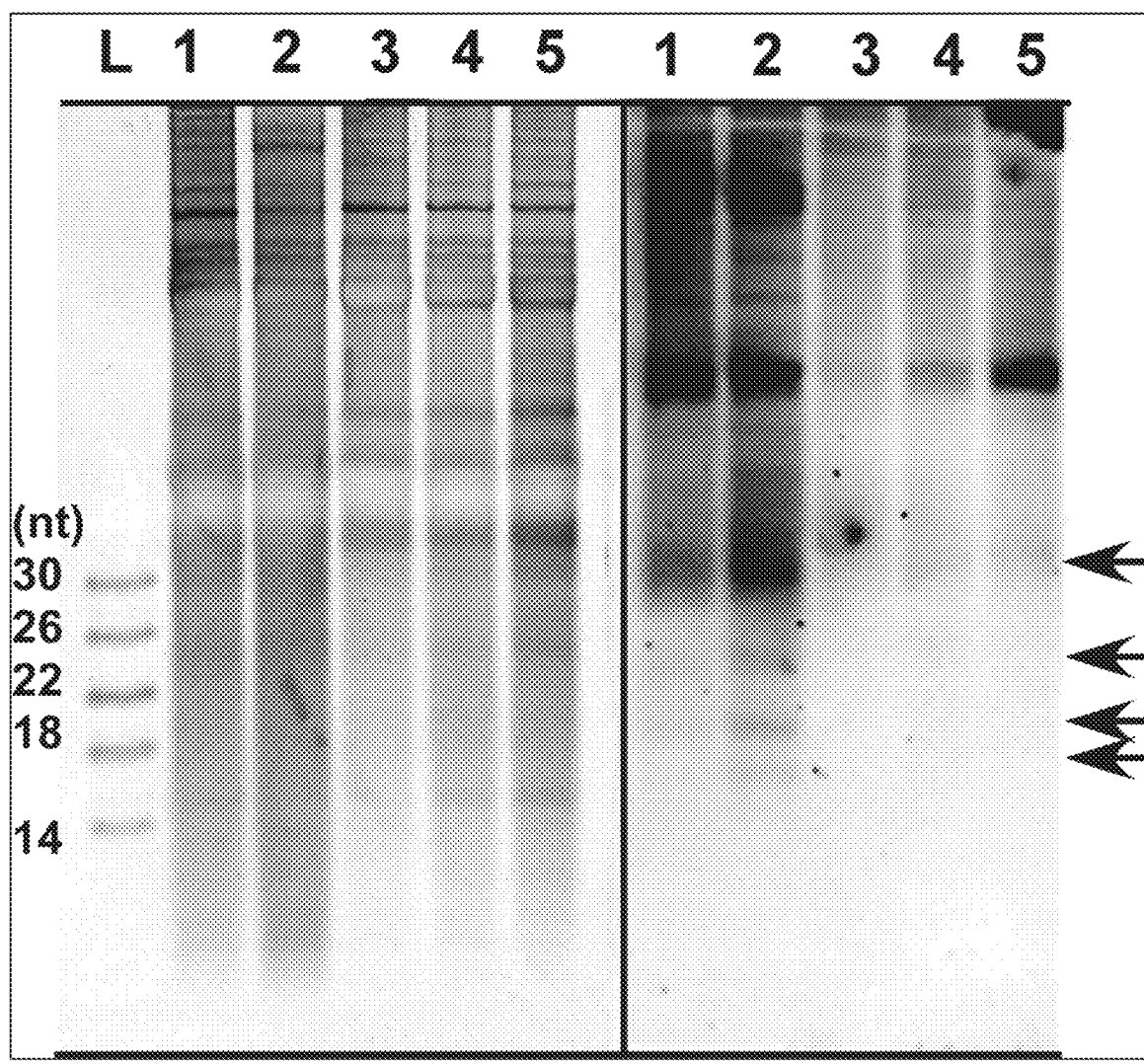
FIG. 5: Accumulation of small RNA in BG322 vp19-fed WSSV infected shrimp. Right panel: RNA electrophoresis on 15% polyacrylamide-8 M urea gel stained by GelRed Nucleic Acid stain (Thermo Fisher Scientific). (L) Takara 14-30 ssRNA Ladder; (1-3) BG322-dsVp19 fed shrimp infected by virus, (4) Control shrimp (no bacteria, no WSSV), (5) nsRNA (dsLuc) fed shrimp infected by WSSV. Left panel: Northern blotting detection of vp19-releted siRNA in shrimp: 1-3, (3) BG322-dsVp19 fed shrimp infected by virus, (4) Control: shrimp (no BG322, no WSSV), (5) Specificity control: BG322-dsLuc fed shrimp infected by WSSV. Arrows indicate vp19-specific bands in siRNA fraction.

As generally demonstrated in FIG. 5, the present inventors showed intensive virus specific smallRNAs in the samples that were prepared from infected shrimp, confirming that viral infection inhibited vp19 gene expression via small interfering RNAs. No prominent small viral RNA was detected in native shrimp that were not infected with WSSV (lane 4). Accumulation of vp19-specific siRNA with sizes ranging from 26 nt to 18 nt was detected in two out of three shrimps (Lanes 1-2). This result demonstrated that that BGG322 vp19 antiviral protection is mediated by an siRNA pathway.

Example 9: *Enterobacter* Ag1 Bacteria are Able to Survive and Stably Colonize Shrimp Intestines In order to check if Ag1 bacteria are able to colonize shrimp intestines, the present inventors performed a colonization experiment. Shrimp were fed by Ag1 labeled by fluorescent EGFP protein for 5 days, afterward bacterial feeding was terminated and shrimp were fed by commercial food. As shown in Table 5 below, concentration of Ag1 in shrimp intestines was measured by plating and cfu counting for 7 weeks post-feeding. Ag1 was present in shrimp intestines during whole experimental time with no noticeable decrease in concentration. The present inventor have concluded that Ag1 bacteria are able to successfully colonize shrimp intestines and therefore are suitable bacterial strain for long-term delivery of therapeutic molecules for shrimp protection.

REFERENCES

The following references are hereby incorporated in their entirety by reference:

[1] Sanjuktha M, Stalin Raj V, Aravindan K, Alavandi S V, Poornima M, Santiago T C. Comparative efficacy of double-stranded RNAs targeting WSSV structural and nonstructural genes in controlling viral multiplication in *Penaeus monodon*. Arch Virol. 2012 May; 157(5):993-8. doi: 10.1007/s00705-012-1258-2. Epub 2012 Feb. 21. PubMed PMID: 22350694.

[2] Kumar, Anil & Allnutt, F C Thomas & Sayre, Richard. (2015). Double Stranded RNA Simultaneously Targeting Four White Spot Syndrome Virus (WSSV) genes provides Protection against WSSV in Litopenaeus vannamei. International Journal of Marine Science and Ocean Technology. 2. 5-10.

[3] Lezzerini M, van de Ven K, Veerman M, Brul S, Budovskaya YV. Specific RNA Interference in *Caenorhabditis elegans* by Ingested dsRNA Expressed in *Bacillus subtilis*. PLoS One. 2015 Apr. 30; 10(4): e0124508. doi: 10.1371/journal.pone.0124508. eCollection 2015. PubMed PMID: 25928543; PubMed Central PMCID: PMC4416053.

[4] Durand, S. V. and Lightner, D. V. (2002), Quantitative real time PCR for the measurement of white spot syndrome virus in shrimp. Journal of Fish Diseases, 25: 381-389. doi:10.1046/j.1365-2761.2002.00367.x.

[5] Chakraborty A., Otta S. K., Kumar B. J. S., Hossain M. S., Karunasagar I., Venugopal M. N., Karunasagar I., Prevalence of white spot syndrome virus in wild crustaceans along the coast of India, Curr. Sci. (2002) 82:1392-1397.).

[6] Nguyen D V, Christiaens O, Bossier P and Smagghe G (2016) RNA interference in shrimp and potential applications in aquaculture. *Reviews in Aquaculture* (2016) 0: 1-12. doi: 10.1111/raq.12187.

[7] Sanchez-Martinez J. G., Aguirre-Guzman G., Mejia-Ruiz H., White spot syndrome virus in cultured shrimp: a review, Aquac. Res. (2007) 38:1339-1354.

[8] Flegel T. W., Nielsen L., Thamavit V., Kongtim S., Pasharawipas T., Presence of multiple viruses in non-diseased, cultivated shrimp at harvest, Aquaculture (2004) 240:55-68.

[9] Hoa T., Hodgson R., Oanh D., Phuong N., Preston N., Walker P., Genotypic variations in tandem repeat DNA segments between ribonucleotide reductase subunit genes of white spot syndrome virus (WSSV) isolates from Vietnam, in: Walker P., Lester R., Reantaso M. (Eds.), Diseases in Asian Aquaculture, Asian Fisheries Society, Manila, 2005, pp. 395-403.

[10] Ma, D.; Hu, Y.; Wang, J.; Ye, S. & Li, A. (2006). Effects of antibacterials use in aquaculture on biogeochemical processes in marine sediment. The Science of the Total Environment, vol. 367, No. 1, pp. 273-277.

[11] Martinez Cruz, Patricia et al. "Use of Probiotics in Aquaculture." ISRN Microbiology 2012 (2012).

[12] Kobayashi, M. & Brummett, R. 2014. Disease management in aquaculture. In: Forum for Agricultural Risk Management in Development.

[13] Walker, Peter J., and James R. Winton. "Emerging Viral Diseases of Fish and Shrimp." Veterinary Research 41.6 (2010).

TABLES

TABLE 1

Fluorescence load in intestines of shrimp fed by GFP-expressing BG322

| Group | Fluorescent load, 5 days, cfu/g | Fluorescent load, 10 days, cfu/g |
|---|---|---|
| shrimp fed by BG322-GFP | 1.1E+06 | 2.1E+05 |
| shrimp fed by commercial feed | 0 | 0 |

TABLE 2

Primers used in qPCR reaction

| Name | Sequence |
|---|---|
| WSSV1011 | TGGTCCCGTCCTCATCTCAG |
| WSSV1079 | GCTGCCTTGCCGGAAATTA |

TABLE 3

Oligonucleotides used in micro RNA Northern blot analysis and complimentary to dsRNA vp19

| Name | DNA sequence |
|---|---|
| VP19-1 | GCCACCACGACTAACACTCTTCCTTTCGGC AGGACCGGAGCCCAGGCCGCTGGCCCTTCT |
| VP19-2 | AGACCCATGCGAGCCATAGACATGGAGCCT TCAAGATCTTCCATGGTGTAAGAAGGGCCA |
| VP19-3 | GCATGGGTCTCTTTTTGATCGTTGCTATCT CAATTGGTATCCTCGTCCTGGCCGTCATGA |
| VP19-4 | GTCCTTATCAGTGTCAGAATCGCTGTCCTT CTTTGGTCCCATCCATACATTCATGACGGC |
| VP19-5 | TGATAAGGACACCGATGATGATGACGACAC TGCCAACGATAACGATGATGAGGACAAATA |
| VP19-6 | ACAGAAGAGCGGACCCAGCCAGAAGCATCA TATCCCTGGTCCTGTTCTTATATTTGTCCT |
| VP19-7 | GGCTGGGTCCGCTCTTCTGTTCCTCGTTTC CGCCGCCACCGTTTTTATGTCTTACCCCAA |

TABLE 4

Target pathogens in poultry populations

| Poultry | Viral diseases | Fungal diseases | Parasitic diseases |
|---|---|---|---|
| Chickens Turkeys Ducks | Avian influenza (has multiple strains or types, and is divided into three types: A, B, and C; H5N1 (genus: *Influenzavirus* A) can cause a 90-100% mortality) | Aspergillosis (genus: *Aspergillus*) | Coccidiosis (genus: *Eimeria*) |
| | Newcastle Disease (genus: *Avulavirus*) Poxvirus diseases (mainly genera: *Parapoxvirus, orthopoxvirus, yatapoxvirus, molluscipoxvirus*) | Candidiasis (genus: *Candida*) | Ascaridia galli (genus: *Ascaridia*) Blackhead (genus: *Histomonas*) |
| | Infectious bronchitis virus (IBV) (genus: *Gammacoronavirus*) | | Mites (genus: *Dermanyssus*) |
| | Laryngotracheitis (genus: *Iltovirus*) Marek's Disease (genus: *Mardivirus*) Eastern Equine Encephalitis (genus: *Alphavirus*) Hemorrhagic enteritis (genus: *Siadenovirus*) Viral arthritis (genus: *Reovirus*) | | Lice (genus: *Menophon*) |

TABLE 5

Target pathogens in bee populations

| Bees (Apis Mellifera) | Viral diseases | Fungal diseases | Parasitic diseases |
|---|---|---|---|
| | Dicistroviruses: | Nosema apis-causing nosemosis, the most common adult honey bees disease. | Varroa mite (Varroa desfructor). |
| | Israeli acute paralysis virus (CCD (Colony Collapse Syndrom)) | Ascosphaera apis (causing Chalkbrood disease) | Honey bee tracheal mites (Acarapis woodi) |
| | Kashmir bee virus (CCD) | Aspegillus spp (causing Stonebrood disease) | Small hive beetles (Aethina tumida) colonies damage in non-apis bees (bumble bees and stingless bees) |
| | Acute bee paralysis virus (CCD) | | Tropilaelaps mites (Tropilaelaps mercedesae) |
| | Black queen cell virus (affect pupae but not adults) | | Wax moth (Pyralidae: Galleria Mellonela and Achroia grisella) |
| | Aphid lethal paralysis virus (possibly CCD) Big sioux river virus (possibly CCD) Iflaviruses: Deformed wing virus Kakugo virus Varroa destructor virus-1 Sacbrood virus Thai/Chinese sacbrood virus Slow bee paralysis virus Baculovirus: Apis iridescent virus (CCD) | | |

TABLE 5-continued

Target pathogens in bee populations

| Bees (Apis Mellifera) | Viral diseases | Fungal diseases | Parasitic diseases |
|---|---|---|---|
| | Unclassified viruses: Cloudy wing virus Bee virus-X Bee virus-Y Lake Sinai virus-1 Lake Sinai virus-2 | | |

TABLE 6

Target pathogens in mammal populations
Mammal Diseases

Bluetongue Virus (BTV): Affects sheep, goats, deer and cattle
Bovine Viral Diarrhoea (BVD): Cattle and other ruminants
Calf Pneumonia: Caused by bovine Respiratory Syncytial Virus (bRSV), Parainfluenza III Virus (PI3)
Infectious Bovine Rhinotracheitis (IBR): Caused by Bovine Herpesvirus-1 (BHV-1)
Trypanosomosis (Sleeping disease): Affects both human and animals Transmitted through tse-tse fly by flagellated protozoan parasites. The most economically important livestock disease of Africa
Foot-and-mouth disease Virus (FMDV): Highly contagious viral disease that affects cattle and swine. It also affects sheep, goats, deer, and other cloven-hoofed ruminants
Rift Valley Fever Virus: viral disease of cattle and sheep. It is spread through infected mosquitoes. It can spread to humans either as airborne and/or by consuming raw milk, handling undercooked meat.
Rotaviral Diarrhoea: Caused by bovine Rotavirus
Parasitic gastro-enteritis (PGE or Gut worms): Affect cattle and is spread through parasites (abomasal worms)
Anaplasmosis: Vector-borne, infectious blood disease in cattle caused by the rickettsial parasites Anaplasma marginale and Anaplasma centrale. It is also known as yellow-bag or yellow-fever
Bovine Anaemia: Benign theileriosis is a tick-borne disease caused by intracellular blood parasites belonging to the Theileria orientalis group (BATOG)
Bovine Babesiosis (BB) (Redwater, Tick Fever): Tick-borne disease of cattle. Caused by single-cell parasites mainly babesia bovis and babesia bigemina, with Rhipicephalus ticks being the major vector
Rabies (Rabies Virus): Affects cattles and other ruminants It is transmitted through the biting of infected animals such as foxes, dogs, skunks and raccoons, but mostly by bat carrying rabies
Neosporosis: Caused by the protozoan Neospora caninum. Affects cattle and sheep. Hosts are canids such as dogs and foxes
Schmallenberg Virus (SBV): New emerging disease. Affects cattle, bison, sheep and goats. Transmitted through midges and vertically from dam to offspring
Epizootic Hemorrhagic Disease Virus (EHDV): Most important infectious disease of white-tailed deer in US. It affects also antelope, mule and other deer species. Cattles are affected uncommonly. It is spread by biting flies (midges, gnats)
Lice: Affects cattle and other ruminants. Two types of lice, biting and sucking lice
Mange: Cattles and other ruminants are infected by mites
Pseudocowpox: Caused by a parapox virus. Most common infectious cause of teat disease in cattle
Ringworm: Skin disease affecting cattles and other ruminants It is caused by Trichophyton verrucosum fungi
Ulcerative mammillitis. Affects cattle. Caused by a herpes virus (BHV-2)
Orf disease: Affects primarily sheep and goats. Caused by a parapox virus
Toxoplasmosis: Affects sheep. Caused by the Toxoplasma gondii parasite.
Coccidiosis: Affects cattle, sheep, chicken, dogs. Caused by Coccidian parasites
Myiasis: Parasitic infestation of a live mammal by fly larvae (maggots).

TABLE 6-continued

Target pathogens in mammal populations
Mammal Diseases

Affects a wide range of mammals such as humans, sheep, horse, rabbit
Louping ill: Acute, tick-transmitted viral disease that affects goats, horses, dogs, pigs, sheep, cattle. Caused by louping ill virus
Echinococcosis: Affects sheep goats, cattle, swine, kangaroos, canids such as dogs and foxes, cats and wild felids. Parasitic disease caused by infection with tiny tapeworms of the genus *Echinococcus*
Fasciolosis: Parasitic worm infection caused by the common liver fluke Fasciola hepatica as well as by Fasciola gigantica. Affects human, sheep and cattle. It is a plant-borne zoonosis
Coenurosis: Parasitic infection that develops in the intermediate hosts of some tapeworm species (*Taenia multiceps, T. serialis, T. brauni*, or *T. glomerata*) and are caused by the coenurus, the larval stage of these worms. Affects sheep and other ungulates but also humans
Caprine arthritis and encephalitis Virus (CAEV): Affects goats
Chagas (TRYPANOSOMA CRUZI): Affects human, horses, cattle and goats. Caused by the parasites trypanosomes
Myxomatosis: Caused by Myxoma virus, transmitted through insect (mosquito, fly, fur mite) bites. Affects rabbits
Ear mites (canker): Affect rabbits. Caused by the mite Psoroptes cuniculi.
Encephalitozoon Cuniculi: Affect rabbits. Caused by single-cell protozoan parasite
Fleas: Ectoparasites
Rabbitpox: Affects rabbits. Caused by rabbitpox virus (RPXV)
Viral Haemorrhagic Disease: Also known as rabbit Haemorrhagic Disease (RHD). Caused by a calicivirus. Affects rabbits
Swine Influenza: Affects pigs. Cause by Swine Influenza virus (SIV)
Japanese B Encephalitis Virus (JE): Affects pigs, transmitted through mosquitoes
Trichinosis: Parasitic disease caused by roundworms of Trichinella. Affects pigs
Encephalomyocarditis Virus (EMCV): Affects pigs, transmitted through rats
Swine pox: Caused by Swine pox virus, affects pigs
Porcine Parvovirus Infection (PPV): Most common and important cause of infectious infertility in pigs
Porcine Respiratory Corona Virus Infection (PRCV)
Porcine Cytomegalovirus Infection (PCMV)
Transmissible Gastro Enteritis (TGE): Caused by a coronavirus. Affects pigs
Enteroviruses, SMEDI: gut-borne viruses. Affects pigs
Aujeszky's disease (AD): Caused by a herpes virus, affects pigs
Nipah virus disease: Causes death both in humans and pigs. New disease, first identified in Malaysia in 1998. Caused by a previously unknown pammyxovirus
Swine Fevers; African, Classical, Hog Cholera Viruses: Affects pigs
Teschen Disease: Caused by a porcine enterovirus serotype 1

TABLE 5

Cfu counting of Ag1 from shrimp intestines, weeks post-feeding

| time postfeeding | cfu/gm |
|---|---|
| 0 | 4.8E+06 |
| 1 week | 9.2E+06 |
| 2 weeks | 4.5E+07 |
| 3 weeks | 4.2E+05 |
| 4 weeks | 3.3E+05 |
| 5 weeks | 6.4E+07 |
| 7 weeks | 1.6E+06 |

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

DNA
dsWsv477
Artificial

SEQ ID NO. 1

ATGTATATCTTCGTCGAAGGTTCCCCCCTCACAGGGAAGAGTTCATGGATGTCCAAGTTGATAG

ATACAGGATCATGTGGAATGTCTTTCCTCAATTTTCTTCGTATGAACACTTCTGACTACTACAA

CTGGCCTGCCGAAATCGGGACAGAACATCTCCAGTTAGGTTTCAGAGAAACCAGAGTGGTGGAT

GGAATGTTTGAACCTGTCCTAAAGACCTTTGTCGACTCGTGGAAGAAAGAGCAAGGAAAAGAGA

GTTTGAAGGAATATCTGGACTACAACGGCCAAGTCATGGAGATCTACATCGCAGAATGGTTGAG

ACAAAGGCCACTAGCCTTCCACGTGTTTACCTATACAGATGAAGCTGTCAAGAGTGGATTCTTG

AACGAGGAGGATCTAGATATGGATACTGCAACCAAGTGGATGGCTGAAATTATTAGAGAAGA

GGGGCAATATTCAAGAAATAAAAGTGACCCCTAGAGTAGTCTTCAATGGCAATGGTTGTAGTGC

ATGTTTCTCTAACACTAAGAGAAACTTGTATAACTTTGGAACAAACTATAACAATGTTGTACAT

TGTGATTTGTTGTGCCCTTTTGCAAGGCATAGGATTGTACATTTCTTATAA

DNA
dsVp28
Artificial

SEQ ID NO. 2

TCACTCTTTCGGTCGTGTCGGCCATCCTCGCCATCACTGCTGTGATTGCTGTATTTATTGTGAT

TTTTAGGTATCACAACACTGTGACCAAGACCATCGAAACCCACACAGGCAATATCGAGACAAAC

ATGGATGAAAACCTCCGCATTCCTGTGACTGCTGAGGTTGGATCAGGCTACTTCAAGATGACTG

ATGTGTCCTTTGACAGCGACACCTTGGGCAAAATCAAGATCCGCAATGGAAAGTCTGATGCACA

GATGAAGGAAGAAGATGCGGATCTTGTATCACTCCCGTGGAGGGCCGAGCACTCGAAGTGACTG

TGGGGCGGAATCTCACCTTTGAGGGGACATTCAAGGTGTGGAACAACACATCAAGAAAGATCAA

CATCACTGGTATGCAGATGGTGCCAAAGATTAACCCATCAAAGGCCTTTGTCGGTAGCTCCAAC

ACCTCCTCCTTCACCCCCGTCTCTATTGATGAGGATGAAGTTGGCACCTTTGTGTGTGGTACCA

CCTTTGGCGCACCAATTGCAGCTACCGCCGGTGGAAATCTTTTCGACATGTACGTGCACGTCAC

CTACTCTGGCACTGAGACCGAGTAA

DNA
dsVp19
Artificial

SEQ ID NO. 3

GCCACCACGACTAACACTCTTCCTTTCGGCAGGACCGGAGCCCAGGCCGCTGGCCCTTCTTACA

CCATGGAAGATCTTGAAGGCTCCATGTCTATGGCTCGCATGGGTCTCTTTTTGATCGTTGCTAT

CTCAATTGGTATCCTCGTCCTGGCCGTCATGAATGTATGGATGGGACCAAAGAAGGACAGCGAT

TCTGACACTGATAAGGACACCGATGATGATGACGACACTGCCAACGATAACGATGATGAGGACA

AATATAAGAACAGGACCAGGGATATGATGCTTCTGGCTGGGTCCGCTCTTCTGTTCCTCGTTTC

CGCCGCCACCGTTTTTATGTCTTACCCCAA

DNA
dsLUC
Artificial

SEQ ID NO. 4

ACAGCCTGGGCATCAGCAAGCCCACCATCGTGTTCAGCAGCAAGAAGGGCCTGGACAAAGTCAT

CACCGTGCAGAAAACCGTGACCACCATCAAGACCATCGTGATCCTGGACAGCAAGGTGGACTAC

CGGGGCTACCAGTGCCTGGACACCTTCATCAAGCGGAACACCCCCCCTGGCTTCCAGGCCAGCA

GCTTCAAGACCGTGGAGGTGGACCGGAAAGAACAGGTGGCCCTGATCATGAACAGCAGCGGCAG

CACCGGCCTGCCCAAGGGCGTGCAGCTGACCCACGAGAACACCGTGACCCGGTTCAGCCACGCC

AGGGACCCCATCTACGGCAACCAGGTGTCCCCCGGCACCGCCGTGCTGACCGTGGTGCCCTTCC

ACCACGGCTTCGGCATGTTCACCACCCTGGGCTACCTGATCTGCGGCTTCCGGGTGGTGATGCT

-continued

```
GACCAAGTTCGACGAGGAAACCTTCCTGAAAACCCTGCAGGACTACAAGTGCACCTACGTGATT

CTGGTGCCCACCCTGTTCGCCATCCTGAACAAGAGCGAGCTGCTGACA
```

Amino Acid
vp19
White spot syndrome virus
SEQ ID NO. 5

```
MATTTNTLPFGRTGAQAAGPSYTMEDLEGSMSMARMGLFLIVAISIGILVLAVMNVWMGPKKDS

DSDTDKDTDDDDDTANDNDDEDKYKNRTRDMMLLAGSALLFLVSAATVFMSYPKRRQ
```

DNA
vp19
White spot syndrome virus
SEQ ID NO. 6

```
ATGGCCACCACGACTAACACTCTTCCTTTCGGCAGGACCGGAGCCCAGGCCGCTGGCCCTTCTT

ACACCATGGAAGATCTTGAAGGCTCCATGTCTATGGCTCGCATGGGTCTCTTTTTGATCGTTGC

TATCTCAATTGGTATCCTCGTCCTGGCCGTCATGAATGTATGGATGGGACCAAAGAAGGACAGC

GATTCTGACACTGATAAGGACACCGATGATGATGACGACACTGCCAACGATAACGATGATGAGG

ACAAATATAAGAACAGGACCAGGGATATGATGCTTCTGGCTGGGTCCGCTCTTCTGTTCCTCGT

TTCCGCCGCCACCGTTTTTATGTCTTACCCCAAGAGGAGGCAGTAA
```

Amino Acid
vp28
White spot syndrome virus
SEQ ID NO. 7

```
VTKTIETHTDNIETNMDENLRIPVTAEVGSGYFKMTDVSFDSDTLGKIKIRNGKSDAQMKEEDA

DLVITPVEGRALEVTVGQNLTFEGTFKVWNNTSRKINITGMQMVPKINPSKAFVGSSNTSSFTP

VSIDEDEVGTFVCGTTFGAPIAATAGGNLFDMYVHVTYSGTETE
```

DNA
vp28
White spot syndrome virus
SEQ ID NO. 8

```
GTGACCAAGACCATCGAAACCCACACAGACAATATCGAGACAAACATGGATGAAAACCTCCGCA

TTCCTGTGACTGCTGAGGTTGGATCAGGCTACTTCAAGATGACTGATGTGTCCTTTGACAGCGA

CACCTTGGGCAAAATCAAGATCCGCAATGGAAAGTCTGATGCACAGATGAAGGAAGAAGATGCG

GATCTTGTCATCACTCCCGTGGAGGGCCGAGCACTCGAAGTGACTGTGGGGCAGAATCTCACCT

TTGAGGGAACATTCAAGGTGTGGAACAACACATCAAGAAAGATCAACATCACTGGTATGCAGAT

GGTGCCAAAGATTAACCCATCAAAGGCCTTTGTCGGTAGCTCCAACACCTCCTCCTTCACCCCC

GTCTCTATTGATGAGGATGAAGTTGGCACCTTTGTGTGTGGTACCACCTTTGGCGCACCAATTG

CAGCTACCGCCGGTGGAAATCTTTTCGACATGTACGTGCACGTCACCTACTCTGGCACTGAGAC

CGAG
```

Amino Acid
Wsv477
White spot syndrome virus
SEQ ID NO. 9

```
MYIFVEGSPLTGKSSWMSKLIDTGSCGMSFLNFLRMNTSDYYNWPAEIGTEHLQLGFRETRVVD

GMFEPVLKTFVDSWKKEQGKESLKEYLDYNGQVMEIYIAEWLRQRPLAFHVFTYTDEAVKSGFL

NEEDLDMDTATKWMAEIIREKRGNIQEIKVTPRVVFNGNGCSACFSNTKRNLYNFGTNYNNVVH

CDLLCPFARHRIVHFL
```

DNA
Wsv477
White spot syndrome virus
SEQ ID NO. 10

```
ATGTATATCTTCGTCGAAGGTTCCCCCCTCACAGGGAAGAGTTCATGGATGTCCAAGTTGATAG

ATACAGGATCATGTGGAATGTCTTTCCTCAATTTTCTTCGTATGAACACTTCTGACTACTACAA
```

```
CTGGCCTGCCGAAATCGGGACAGAACATCTCCAGTTAGGTTTCAGAGAAACCAGAGTGGTGGAT

GGAATGTTTGAACCTGTCCTAAAGACCTTTGTCGACTCGTGGAAGAAAGAGCAAGGAAAAGAGA

GTTTGAAGGAATATCTGGACTACAACGGCCAAGTCATGGAGATCTACATCGCAGAATGGTTGAG

ACAAAGGCCACTAGCCTTCCACGTGTTTACCTATACAGATGAAGCTGTCAAGAGTGGATTCTTG

AACGAGGAGGATCTAGATATGGATACTGCAACCAAGTGGATGGCTGAAATTATTAGAGAGAAGA

GGGGCAATATTCAAGAAATAAAAGTGACCCCTAGAGTAGTCTTCAATGGCAATGGTTGTAGTGC

ATGTTTCTCTAACACTAAGAGAAACTTGTATAACTTTGGAACAAACTATAACAATGTTGTACAT

TGTGATTTGTTGTGCCCTTTTGCAAGGCATAGGATTGTACATTTCTTATAA
```

---

What is claimed is:

1. A composition for the biocontrol of white spot syndrome comprising:
a genetically modified probiotic bacteria that expresses at least one heterologous inhibitory polynucleotide encoded by a nucleic acid selected from the group consisting of: SEQ ID NO. 1, SEQ ID NO. 2, and SEQ ID NO. 3, wherein said at least one heterologous inhibitory polynucleotide is a double stranded RNA polynucleotide molecule (dsRNA) that targets an essential gene in a white spot syndrome virus (WSSV), wherein said essential gene is selected from the group consisting of: wsv477, vp28, and vp19.

2. The composition of claim 1, wherein said genetically modified probiotic bacteria comprises a genetically modified probiotic bacteria selected from the group consisting of: *Bacillus subtilis*, and *Enterobacter*.

3. The composition of claim 1, wherein said genetically modified probiotic bacteria comprises an RNaseIII deficient genetically modified probiotic bacteria.

4. The composition of claim 1, wherein said genetically modified probiotic bacteria is added to a commercial feed forming a treated feed for an aquatic animal that is infected with WSSV, or susceptible to infection by WSSV.

5. The composition of claim 4, wherein said at least one heterologous inhibitory polynucleotide selected from the group of nucleic acid sequences consisting of SEQ ID NO. 1, SEQ ID NO. 2, and SEQ ID NO. 3, comprises at least one heterologous inhibitory polynucleotide selected from the group of nucleic acid sequences consisting of: at least one heterologous inhibitory polynucleotide having 95% homology with SEQ ID NO. 1; at least one heterologous inhibitory polynucleotide having at least 95% homology with SEQ ID NO. 2, and at least one heterologous inhibitory polynucleotide having 95% homology with SEQ ID NO. 3.

6. The composition of claim 5, wherein the biocontrol of white spot syndrome comprises the biocontrol of white spot syndrome in shrimp.

7. The composition of claim 6, wherein said shrimp comprise shrimp raised in an aquaculture environment.

8. The composition of claim 7, wherein said genetically modified probiotic bacteria is transmitted to a shrimp progeny through vertical transmission.

9. The composition of claim 8, and further comprising a therapeutically effective amount of said genetically modified probiotic bacteria administered to said shrimp raised in an aquaculture environment such that said heterologous inhibitory polynucleotide downregulates expression of said essential gene in WSSV and further results in a reduction in mortality due to WSSV in said shrimp raised in an aquaculture environment that are administered a therapeutically effective amount of said probiotic bacteria.

10. A composition for the biocontrol of white spot syndrome in shrimp comprising:

a genetically modified probiotic enteric bacteria that expresses at least one heterologous inhibitory polynucleotide selected from the group nucleic acids sequences consisting of: SEQ ID NO. 1, SEQ ID NO. 2, and SEQ ID NO. 3, wherein said at least one heterologous inhibitory polynucleotide is a double stranded RNA polynucleotide molecule (dsRNA) that targets an essential gene in a white spot syndrome virus (WSSV), wherein said essential gene is selected from the group consisting of: wsv477, vp28, and vp19.

11. The composition of claim 10, wherein said genetically modified probiotic enteric bacteria comprises a genetically modified probiotic enteric bacteria selected from the group consisting of: *Bacillus subtilis*, and *Enterobacter* bacteria.

12. The composition of claim 11, wherein said genetically modified probiotic enteric bacteria comprises an RNaseIII deficient genetically modified probiotic enteric bacteria.

13. The composition of claim 10, wherein said genetically modified probiotic enteric bacteria is added to a commercial shrimp feed forming a treated feed for shrimp that is infected with WSSV, or susceptible to infection by WSSV.

14. The composition of 13, wherein said at least one heterologous inhibitory polynucleotide selected from the group of nucleic acid sequences consisting of SEQ ID NO. 1, SEQ ID NO. 2, and SEQ ID NO. 3, comprises at least one heterologous inhibitory polynucleotide selected from the group consisting of: at least one heterologous inhibitory polynucleotide having 95% homology with SEQ ID NO. 1; at least one heterologous inhibitory polynucleotide having 95% homology with SEQ ID NO. 2, and at least one heterologous inhibitory polynucleotide having 95% homology with SEQ ID NO. 3.

15. The composition of 10, wherein said shrimp comprise shrimp raised in an aquaculture environment.

16. The composition of 15 wherein said genetically modified probiotic enteric bacteria is transmitted to shrimp progeny through vertical transmission.

17. The composition of 16, and further comprising a therapeutically effective amount of said genetically modified probiotic enteric bacteria administered to said shrimp raised in an aquaculture environment such that said heterologous inhibitory polynucleotide downregulating expression of said essential gene in a WSSV, an further results in a reduction in mortality due to WSSV in said shrimp raised in an aquaculture environment.

* * * * *